US007683180B2

(12) United States Patent
Grubbs et al.

(10) Patent No.: US 7,683,180 B2
(45) Date of Patent: Mar. 23, 2010

(54) GROUP 8 TRANSITION METAL CARBENE COMPLEXES AS ENANTIOSELECTIVE OLEFIN METATHESIS CATALYSTS

(75) Inventors: Robert H. Grubbs, South Pasadena, CA (US); Donald W. Ward, Atladena, CA (US); Thomas J. Seiders, San Diego, CA (US); Steven D. Goldberg, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 2014 days.

(21) Appl. No.: 10/124,745

(22) Filed: Apr. 16, 2002

(65) Prior Publication Data

US 2003/0055262 A1 Mar. 20, 2003

Related U.S. Application Data

(60) Provisional application No. 60/284,214, filed on Apr. 16, 2001.

(51) Int. Cl.
*C07F 15/00* (2006.01)
*C07F 7/02* (2006.01)
*B01J 31/00* (2006.01)
*C08F 4/80* (2006.01)

(52) U.S. Cl. .................. 548/103; 556/21; 556/136; 556/137; 585/643; 585/646; 502/152; 502/162

(58) Field of Classification Search ............. 556/21, 556/136, 137; 548/103; 502/152, 162; 585/350, 585/366, 643, 646
See application file for complete search history.

(56) References Cited

U.S. PATENT DOCUMENTS

| | | | |
|---|---|---|---|
| 5,312,940 A | 5/1994 | Grubbs et al. | 556/136 |
| 5,342,909 A | 8/1994 | Grubbs et al. | 526/171 |
| 5,831,108 A | 11/1998 | Grubbs et al. | 556/21 |
| 5,917,071 A | 6/1999 | Grubbs et al. | 556/21 |
| 5,969,170 A | 10/1999 | Grubbs et al. | 556/21 |
| 6,107,420 A | 8/2000 | Grubbs et al. | 526/73 |
| 6,111,121 A | 8/2000 | Grubbs et al. | 556/21 |
| 6,211,391 B1 | 4/2001 | Grubbs et al. | 556/21 |
| 6,271,315 B1 | 8/2001 | Kiessling et al. | 525/326.1 |
| 6,291,616 B1 | 9/2001 | Kiessling et al. | 526/171 |
| 6,409,875 B1 | 6/2002 | Giardello et al. | 156/334 |
| 6,426,419 B1 | 7/2002 | Grubbs et al. | 548/101 |
| 6,521,799 B2 | 2/2003 | Wagener et al. | 568/852 |
| 2001/0006988 A1 | 7/2001 | Kuhnle et al. | 524/127 |
| 2001/0049398 A1 | 12/2001 | Olivier-Bourbigou et al. | 518/715 |
| 2002/0022741 A1 | 2/2002 | Pederson et al. | 560/234 |
| 2002/0107138 A1 | 8/2002 | Hoveyda et al. | 502/152 |
| 2002/0173650 A1 | 11/2002 | Nolan et al. | 546/2 |
| 2002/0177710 A1 | 11/2002 | Grubbs et al. | 540/2 |

FOREIGN PATENT DOCUMENTS

| | | |
|---|---|---|
| DE | 4447066 A1 | 7/1996 |
| EP | 0798041 A1 | 10/1997 |
| JP | 2001-270892 A | 2/2001 |
| WO | WO 00/15339 | 3/2000 |

OTHER PUBLICATIONS

Morrison and Boyd, Organic Chemistry, 3rd Edition, Allyn and Bacon, Inc. (1973), p. 125.*
Adlhart et al. (2000), "Mechanistic Studies of Olefin Metathesis by Ruthenium Carbene Complexes Using Electrospray Ionization Tandem Mass Spectrometry," *J. Am. Chem. Soc.* 122(34):8204-8214.
Alexander et al. (1998), "Catalytic Enantioselective Ring-Closing Metathesis by a Chiral Biphen-Mo Complex," *J. Am. Chem. Soc.* 120(16):4041-4042.
Arduengo (1999), "Looking for Stable Carbenes: The Difficulty in Starting Anew," *Accounts of Chemical Research* 32(11):913-921.
Bianchini et al. (2000), "Cyclopropanation of Styrene with Ethyl Diazoacetate Catalyzed by Chiral and Achiral Ruthenium 2,6-Bis(imino)pyridyl Complexes," *Organometallics* 19(10):1833-1840.
Bourissou et al. (2000), "Stable Carbenes," *Chem. Rev.* 100(1):39-91.
Brown et al. (1978), "Structure of Bis(dimethylphenylphosphine)(ethylene)(carbonyl)dichlororuthenium(II), $RuCl_2(CO)(C_2H_4)(P(CH_3)_2(C_6H_5))_2$, a Six-Coordinate $d^6$ Complex Containing Ethylene as a Ligand," *Inorganic Chemistry* 17(10):2932-2935.
Cefalo et al. (2001), "Enantioselective Synthesis of Unsaturated Cyclic Tertiary Ethers by Mo-Catalyzed Olefin Metathesis," *J. Am. Chem. Soc.* 123(13):3139-3140.
Dias et al. (1997), "Well-Defined Ruthenium Olefin Metathesis Catalysts: Mechanism and Activity," *J. Am. Chem. Soc.* 119(17):3887-3897.
Fürstner (2000), "Olefin Metathesis and Beyond," *Angew. Chem. Int. Ed.* 39:3012-3043.
Grubbs et al. (1998), "Recent Advances in Olefin Metathesis and Its Application in Organic Synthesis," *Tetrahedron* 54:4413-4450.
Hinderling et al. (1998), "Olefin Metathesis of a Ruthenium Carbene Complex by Electrospray Ionization in the Gas Phase," *Angew. Chem., Int. Ed.* 37(19):2685-2689.
Hoveyda et al. (2001), "Catalytic Asymmetric Olefin Metathesis," *Chem. Eur. J.* 7(5):945-950.
Huang et al. (1999), "Olefin Metathesis-Active Ruthenium Complexes Bearing a Nucleophilic Carbene Ligand," *J. Am. Chem. Soc.* 121(12):2674-2678.
Ivin (1998), "Some Recent Applications of Olefin Metathesis in Organic Synthesis: A Review," *Journal of Molecular Catalysis A: Chemical* 133:1-16.

(Continued)

*Primary Examiner*—Porfirio Nazario Gonzalez
(74) *Attorney, Agent, or Firm*—Nixon Peabody LLP; Jeffrey N. Townes

(57) ABSTRACT

The invention pertains to the use of Group 8 transition metal carbene complexes as catalysts for olefin cross-metathesis reactions, and for enantioselective reactions in particular. The synthesis of these complexes and details of their use as catalysts is also provided.

69 Claims, No Drawings

OTHER PUBLICATIONS

Jafarpour et al. (2000), "Simple and Convenient Synthetic Procedure Leading to Ruthenium Olefin Metathesis Catalysts Bearing the N,N-Bis(mesityl)imidazol-2-ylidene (IMes) Ligand," *Organometallics* 19(11):2055-2057.

Kingsbury et al. (1999), "A Recyclable Ru-Based Metathesis Catalyst," *J. Am. Chem. Soc.* 121(4):791-799.

La et al. (1998), "Mo-Catalyzed Asymmetric Synthesis of Dihydrofurans. Catalytic Kinetic Resolution and Enantioselective Desymmetrization through Ring-Closing Metathesis," *J. Am. Chem. Soc.* 120(37):9720-9721.

La et al. (1999), "Tandem Catalytic Asymmetric Ring-Opening Metathesis/Cross Metathesis," *J. Am. Chem. Soc.* 121(49):11603-11604.

Moers et al. (1977), "Cyanoolefin Complexes of Osmium(II)and Ruthenium(II)," *J. Inorg. Nucl. Chem.* 39:591-593.

Randall et al. (1998), "Selective Olefin Metatheses—New Tools for the Organic Chemist: A Review," *Journal of Molecular Catalysis A: Chemical* 133:29-40.

Saba et al. (1991), "One-Pot Synthesis of Cyclic Amidinium Tetrafluoroborates and Hexafluorophosphates; the Simplest Models of $N^5,N^{10}$-Methenyltetrahydrofolate Coenzyme," *Tetrahedron Letters* 32(38):5031-5034.

Sanford et al. (2000), "Ruthenium-Based Four-Coordinate Olefin Metathesis Catalysts," *Angew. Chem. Int. Ed.* 39(19):3451-3453.

Sanford et al. (2001), "New Insights into the Mechanism of Ruthenium-Catalyzed Olefin Metathesis Reactions," *J. Am. Chem. Soc.* 123(4):749-750.

Sanford et al. (2001), "Mechanism and Activity of Ruthenium Olefin Metathesis Catalysts," *J. Am. Chem. Soc.* 123(27):6543-6554.

Scholl et al. (1999), "Increased Ring Closing Metathesis Activity of Ruthenium-Based Olefin Metathesis Catalysts Coordinated with Imidazolin-2-ylidene Ligands," *Tetrahedron Letters* 40:2247-2250.

Scholl et al. (1999), "Synthesis and Activity of a New Generation of Ruthenium-Based Olefin Metathesis Catalysts Coordinated with 1,3-Dimesity1-4,5-dihydroimidazol-2-ylidene Ligands," *Organic Letters* 1(6):953-956.

Schwab et al. (1995), "A Series of Well-Defined Metathesis Catalysts—Synthesis of [RuCl$_2$(=CHR')(PR$_3$)$_2$] and Its Reactions," *Angew. Chem., Int Ed. Engl.* 34:2039-2041.

Schwab et al. (1996), "Synthesis and Applications of RuCl$_2$(=CHR')(PR$_3$)$_2$: The Influence of the Alkylidene Moiety on Metathesis Activity," *J. Am. Chem. Soc.* 118(1):100-110.

Seiders et al. (2001), "Enantioselective Ruthenium-Catalyzed Ring-Closing Metathesis," *Organic Letters* 3(20):3225-3228.

Tallarico et al. (1997), "Ring-Opening Metathesis. A Ruthenium Catalyst Caught in the Act," *J. Am. Chem. Soc.* 119(30):7157-7158.

Trnka et al. (2001), "The Development of L$_2$X$_2$Ru=CHR Olefin Metathesis Catalysts: An Organometallic Success Story," *Acc. Chem. Res.* 34:18-29.

Trnka et al. (2001), "Novel $\eta^3$-Vinylcarbene Complexes Derived from Ruthenium-Based Olefin Metathesis Catalysts," *Organometallics* 20(18):3845-3847.

Ulman et al. (1998), "Relative Reaction Rates of Olefin Substrates with Ruthenium(II) Carbene Metathesis Initiators," *Organometallics* 17(12):2484-2489.

Ulman et al. (1999), "Ruthenium Carbene-Based Olefin Metathesis Initiators: Catalyst Decomposition and Longevity," *J. Org. Chem.* 64(19):7202-7207.

Weatherhead et al. (2000), "Tandem Catalytic Asymmetric Ring-Opening Metathesis/Ring-Closing Metathesis," *J. Am. Chem. Soc.* 122(8):1828-1829.

Weskamp et al. (1998), "A Novel Class of Ruthenium Catalysts for Olefin Metathesis," *Angew. Chem. Int. Ed.* 37(18):2490-2493.

Wolfe et al. (1998), "Rational Development of Practical Catalysts for Aromatic Carbon-Nitrogen Bond Formatio%" *Acc. Chem. Res.* 31(12):805-818.

Wolfe et al. (2000), "Scope and Limitations of the Pd/BINAP-Catalyzed Amination of Aryl Bromides," *J. Org. Chem.* 65(4):1144-1157.

Yang et al. (1999), "Palladium-Catalyzed Amination of Aryl Halides and Sulfonates," *Journal of Organometallic Chemistry* 576:125-146.

Zhu et al. (1999), "Chiral Mo-Binol Complexes: Activity, Synthesis, and Structure. Efficient Enantioselective Six-Membered Ring Synthesis through Catalytic Metathesis," *J. Am. Chem. Soc.* 121(36):8251-8259.

Buchmeiser (2000), "Homogeneous Metathesis Polymerization by Well-Defined Group VI and Group VIII Transition-Metal Alkylidenes: Fundamentals and Applications in the Preparation of Advanced Materials," *Chem. Rev.* 100(4):1565-1604.

\* cited by examiner

GROUP 8 TRANSITION METAL CARBENE COMPLEXES AS ENANTIONSELECTIVE OLEFIN METATHESIS CATALYSTS

CROSS-REFERENCE TO RELATED APPLICATIONS

This application claims priority under 35 U.S.C. §119(e)(1) to provisional U.S. patent application Ser. No. 60/284,214, filed Apr. 16, 2001.

ACKNOWLEDGEMENT OF GOVERNMENT SUPPORT

This invention was developed with U.S. Government support under grant number GM31332 awarded by the National Institutes of Health.

TECHNICAL FIELD

This invention relates generally to method for carrying out an olefin metathesis reaction using a chiral Group 8 transition metal complex as a catalyst. More particularly, the invention relates to methods for carrying out enantioselective reactions using the aforementioned catalyst.

BACKGROUND OF THE INVENTION

Over the past decade, olefin metathesis has emerged as a powerful carbon-carbon bond-forming reaction that is widely used in organic synthesis and polymer science (Trnka et al., *Acc. Chem. Res.* 34:18-29 (2001); Fürstner et al., *Angew. Chem., Int. Ed.* 39:3012-3043 (2000); Ivin et al., *J. Mol. Catal. A: Chem.* 133:1-16 (1998); Randall et al., *J. Mol. Catal. A: Chem.* 133:29-40 (1998); and Grubbs et al., *Tetrahedron* 54:4413-4450 (1998)). "Olefin metathesis," as is understood in the art, refers to the metal-catalyzed redistribution of carbon-carbon bonds.

A major advance in this field was the development of chiral molybdenum catalysts that exhibit high enantioselectivity in a variety of ring-closing (Alexander et al., *J. Am. Chem. Soc.* 120:4041-4042 (1998); La et al., *J. Am. Chem. Soc.* 120:9720-9721 (1998); Cefalo et al., *J. Am. Chem. Soc.* 123:3139-3140 (2001); and Zhu et al., *J. Am. Chem. Soc.* 121:8251-8259 (1999)) and ring-opening (La et al., *J. Am. Chem. Soc.* 121:11603-11604 (1999); and Weatherhead et al., *J. Am. Chem. Soc.* 122:1828-1829 (2000)) metathesis reactions. See Hoveyda et al., *Chem. Eur. J.* 7:945-950 (2001) for a general review of molybdenum-catalyzed enantioselective metathesis. However, these molybdenum-based systems require specific substrate-to-catalyst matching, necessitating individual optimization of any one metathesis reaction and the availability of a number of catalysts.

Over two decades of intensive research effort has culminated in the discovery of well-defined ruthenium and osmium carbenes that are highly active olefin metathesis catalysts and stable in the presence of a variety of functional groups.

These ruthenium and osmium carbene complexes have been described in U.S. Pat. Nos. 5,312,940, 5,342,909, 5,831,108, 5,969,170, 6,111,121, and 6,211,391, all to Grubbs et al. The ruthenium and osmium carbene complexes disclosed in these patents all possess metal centers that are formally in the +2 oxidation state, have an electron count of 16, and are penta-coordinated. These catalysts are of the general formula (I):

where M is a Group 8 transition metal such as ruthenium or osmium, X and X' are anionic ligands, L and L' are neutral electron donors, and R and R' are specific substituents, e.g., one may be H and the other may be a substituted or unsubstituted hydrocarbyl group such as phenyl or $-C=C(CH_3)_2$. Such complexes have been shown to be useful in catalyzing a variety of olefin metathesis reactions, including ring opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions. Their broad range of applications is due in large part to their excellent compatibility with various functional groups and relatively high tolerance to moisture, air, and other impurities (Schwab et al., *Angew. Chem., Int. Ed. Engl.* 34:2039-2041(1995); Schwab et al., *J. Am. Chem. Soc.* 118:100-110 (1996); Ivin, *J. Mol. Cat. A-Chem.* 133:1-16 (1998); Grubbs et al., *Tetrahedron.* 54:4413-4450 (19998); and Randall et al., *J. Mol. Cat. A-Chem.* 133, 29-40 (1998)). However, as has been recognized by those in the field, the compounds display relatively low thermal stability, decomposing at relatively low temperatures in solution. Jafarpour et al., *Organometallics* 19(11): 2055-2057 (2000). The decomposition is largely limited to solutions of the catalyst as dry (solvent-free) solid catalysts are fairly stable.

For the most part, such metathesis catalysts have been prepared with phosphine ligands, e.g., tricyclohexylphosphine or tricyclopentylphosphine, exemplified by the well-defined, metathesis-active ruthenium alkylidene complexes (II) and (III):

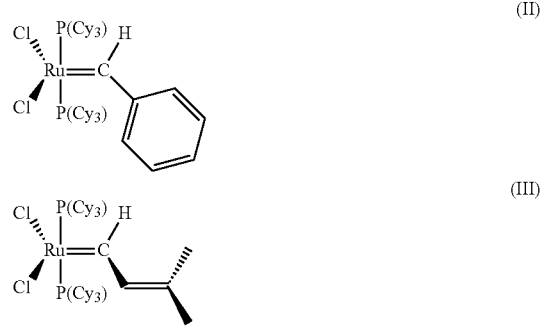

wherein "Cy" is a cycloalkyl group such as cyclohexyl or cyclopentyl. See Grubbs et al., U.S. Pat. No. 5,917,071 and Trnka et al., supra. To increase the reactivity of ruthenium-based catalysts, replacement of one of the phosphine ligands with a 1,3-disubstituted-4,5-dihydro-(4,5-disubstituted)-imidazole-2-ylidene, such as 1,3-dimesityl-4,5-dihydroimidazol-2-ylidene, furnishes more active catalysts, apparently due to a more electron-rich ruthenium metal center (Scholl et al., *Tetrahedron Lett.* 40:2247-2250 (1999) and Scholl et al., *Org. Lett.* 1:953-956 (1999)).

From these studies, it became apparent that highly basic N-heterocyclic carbene ligands are an excellent ligand set for improvement in olefin metathesis reactivity, and are superior alternatives to phosphines (Trnka et al., supra; Bourissou et al. *Chem. Rev.* 100:39-91 (2000); Scholl et al., *Tet. Lett.* 40:2247-2250 (1999); Scholl et al., *Organic Lett.* 1(6):953-956 (1999); and Huang et al., *J. Am. Chem. Soc.* 121:2674-2678 (1999)). N-heterocyclic carbene ligands offer many advantages, including readily tunable steric bulk, vastly increased electron donor character, and compatibility with a variety of metal species. In addition, replacement of one of the phosphine ligands in these complexes significantly improves thermal stability in solution. The vast majority of research on these carbene ligands has focused on their generation and isolation, a feat finally accomplished by Arduengo and coworkers within the last ten years (see, e.g., Arduengo et al., *Acc. Chem. Res.* 32:913-921 (1999)). Four representative second generation catalysts are the ruthenium complexes (IVA), (IVB), (VA) and (VB):

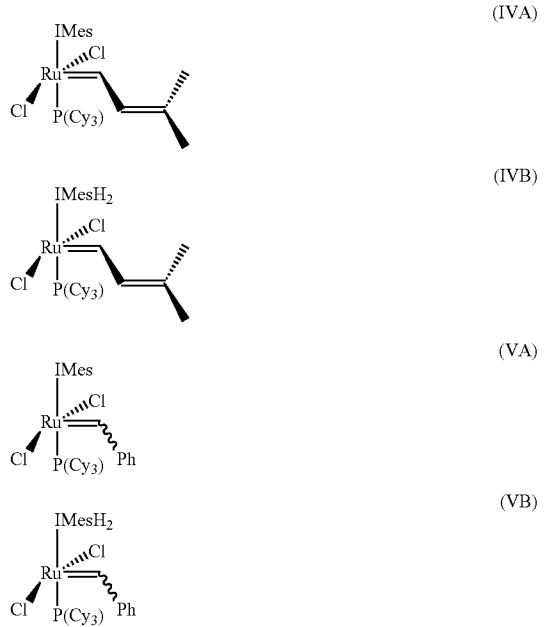

In the above structures, Cy is as defined previously, Ph represents phenyl, "IMes" represents 1,3-dimesityl-imidazol-2-ylidene:

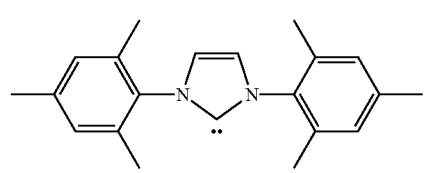

and "IMesH$_2$" represents 1,3-dimesityl-4,5-dihydroimidazol-2-ylidene:

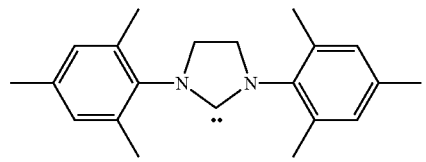

Other ruthenium-based olefin metathesis catalysts formed with N-heterocyclic carbene ligands are known.

These transition metal carbene complexes, particularly those containing a ligand having the 4,5-dihydroimidazol-2-ylidene structure such as in IMesH$_2$, have been found to address a number of previously unsolved problems in olefin metathesis reactions, particularly cross-metathesis reactions. However, in all previous applications of Group 8-catalyzed olefin metathesis, such as ring-closing metathesis, there has been no general method for controlling the enantioselectivity of the catalytic process. Additionally, the molybdenum-based catalysts are limited since these systems lack extensive functional group tolerance and require rigorous exclusion of air and moisture.

Therefore, there is a need for the development of enantioselective metathesis catalysts based on Group 8 transition metals such as ruthenium. The instant invention addresses this need by providing for various novel chiral 1,3-disubstituted-4,5-dihydro-(4,5-disubstituted)-imidazol-2-ylidene ligands and analogs thereof, methods for their synthesis, as well as methods of use in the synthesis of novel chiral Group 8 transition metal complexes useful as olefin metathesis catalysts. The chiral N-heterocyclic carbene (NHC) ruthenium complexes of the invention exhibit high enantioselectivity, for example up to 90% ee in the ring-closing metathesis of achiral trienes. While chiral N-heterocyclic carbene ruthenium complexes have been reported previously (Scholl et al., *Org. Lett.* 1:953-956 (1999) and Weskamp et al., *Angew. Chem. Int. Ed.* 37:2490-2493 (1998)), none report their use in asymmetric metathesis.

SUMMARY OF THE INVENTION

One aspect of the invention pertains to a Group 8 transition metal carbene complex of the formula (VI) and olefin metathesis reactions carried out with this complex:

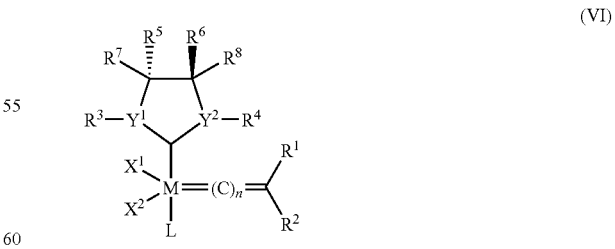

wherein:

M is a Group 8 transition metal;

$X^1$ and $X^2$ are independently selected from the group consisting of anionic ligands and polymers, or $X^1$ and $X^2$ may be taken together to form a cyclic group;

n is an integer from 0-5;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxyl;

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group;

$Y^1$ and $Y^2$ are heteroatoms independently selected from the group consisting of N, O, S, and P, with the proviso that when $Y^1$ or $Y^2$ is O or S, then $R^3$ or $R^4$ is absent;

$R^3$ and $R^4$ are independently selected from the group consisting of hydrogen, functional groups, hydrocarbyl, substituted hydrocarbyl, heteroatom-containing hydrocarbyl, substituted heteroatom-containing hydrocarbyl, and polymers;

$R^5$, $R^6$, $R^7$, and $R^8$ are independently selected from the group consisting of polymers, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, aryl, hydroxyl, sulfhydryl, —(CO)—H, halide, and functional groups;

L is a neutral electron donor ligand, and may or may not be linked to $R^2$, $X^1$, and/or $X^2$ through a spacer moiety; and wherein any two or more of $X^1$, $X^2$, L, $R^1$, $R^2$, $R^3$, $R^4$, $R^5$, $R^6$, $R^7$, and $R^8$ can be taken together to form a chelating multidentate ligand.

Another aspect of the invention pertains to a ruthenium carbene complex of the formula (VII):

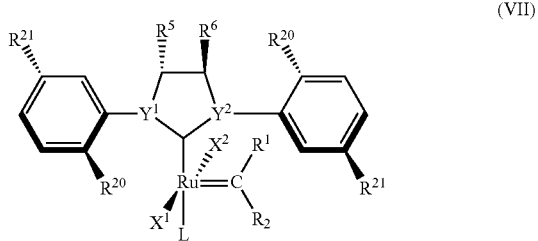

(VII)

wherein:

$X^1$ and $X^2$ are independently selected from the group consisting of anionic ligands and polymers, or $X^1$ and $X^2$ may be taken together to form a cyclic group;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxyl;

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group;

$Y^1$ and $Y^2$ are heteroatoms independently selected from the group consisting of N, O, S, and P, with the proviso that when $Y^1$ or $Y^2$ is O or S, then the appended aryl group is absent;

$R^5$ and $R^6$ are independently selected from the group consisting of polymers, hydrogen, hydrocarbyl, substituted hydrocarbyl, heteroatom-containing hydrocarbyl, substituted heteroatom-containing hydrocarbyl, functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

$R^{20}$ and $R^{21}$ are independently selected from the group consisting of hydrogen, $C_{1-20}$ alkyl, substituted $C_{1-20}$ alkyl, perfluoronated $C_{1-20}$ alkyl, $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl, $C_{5-30}$ alkaryl, and halo; and L is a neutral electron donor ligand.

Yet another aspect of the invention pertains to a method of controlling the enantioselectivity of an olefin metathesis reaction comprising catalyzing the reaction with a chiral Group 8 transition metal carbene complex of formula (VI).

DETAILED DESCRIPTION OF THE INVENTION

The present invention is addressed to the aforementioned needs in the art, and provides a novel process for using chiral Group 8 transition metal complexes to catalyze a variety of olefin metathesis reactions, including cross-metathesis reactions. The complexes are metal carbenes comprised of a Group 8 transition metal, particularly ruthenium or osmium. Such complexes are highly active catalysts of olefin metathesis reactions, including the cross-metathesis reactions described in detail herein.

In contrast to previous catalysts used in olefin cross-metathesis, the present complexes tolerate a greater diversity of functional groups and are more stable to air and moisture. The present complexes allow an olefinic reactant to be substituted with a functional group without compromising the efficiency or selectivity of a metathesis reaction involving that olefin. The present invention also allows the second reactant, i.e., the olefin metathesis partner, to be substituted with a functional group. The functional group may or may not be a ligand for the metal complex; the present method is not limited in this regard.

In addition, due to the stereochemistry of the complexes of the invention, the enantioselectivity of olefin metathesis can now be controlled. In particular, the Group 8 transition metal carbene complexes of the invention find utility in effecting a variety of asymmetric metathesis reactions including, but not limited to, enantioselective ring-closing metathesis, asymmetric desymmetrization of meso-trienes, enantioselective cross-metathesis, enantioselective ring-opening/cross metathesis, enantioselective ring-opening/ring-closing metathesis, and kinetic resolution of racemic mixtures of chiral olefins.

The substitution of a chiral ligand, such as a 1,3-disubstituted-4,5-dihydro-(4,5-disubstituted)-imidazol-2-ylidene, for a phosphine ligand in a bisphosphine-ligated Group 8 alkylidene complex to form the Group 8 transition metal carbene complexes of the invention provides for the generation of a series of novel chiral Group 8 transition metal olefin metathesis complexes. These complexes have been shown to exhibit high enantioselectivity in a variety of olefin metathesis reactions. As catalysts, the complexes exhibit relatively high functional-group tolerance and relatively high stability in the presence of water, oxygen, ionic liquids, protic solvents, and a variety of common impurities. This functional-group tolerance and enhanced stability allow for the effective transformation of substrates inaccessible with previously reported chiral molybdenum metathesis catalysts.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners.

I. Definitions and Nomenclature

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "a solvent" includes a single solvent as well as solvent mixture, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

"Alicyclic" refers to an aliphatic cyclic moiety, which may or may not be bicyclic or polycyclic.

"Alkenyl" as used herein refers to a linear, branched or cyclic hydrocarbon group of about 2-20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain about 2-12 carbon atoms. The term "lower alkenyl" intends an alkenyl group of 2 to 6 carbon atoms, and the specific term "cycloalkenyl" intends a cyclic alkenyl group, preferably having about 5-8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

"Alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing about 1-6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

"Alkoxycarbonyl" refers to the substituent —COOR, where R is an alkyl group as defined herein.

"Alkyl" as used herein refers to a linear, branched or cyclic saturated hydrocarbon group typically although not necessarily containing about 1-20 carbon atoms ($C_{1-20}$ alkyl), such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain about 1-12 carbon atoms and typically about 1-10 carbon atoms. The term "lower alkyl" intends an alkyl group of about 1-6 carbon atoms, and the specific term "cycloalkyl" intends a cyclic alkyl group, typically having about 4-8, preferably about 5-7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

"Alkyldiketonate" refers to an alkyl group as defined herein, having two ketone carbonyl groups. Typically the alkyl will have from 3-30 carbon atoms.

"Alkylene" as used herein refers to a difunctional linear, branched or cyclic alkyl group, where "alkyl" is as defined above.

"Alkylsulfanyl" refers to the group —S—R, where R is an alkyl group.

"Alkylsulfinyl" refers to the group —SO—R, where R is an alkyl group.

"Alkylsulfonato" refers to the group —S(O)$_3$—R, where R is an alkyl group.

"Alkylsulfonyl" refers to the group —S(O)$_2$—R, where R is an alkyl group.

"Alkynyl" as used herein refers to a linear or branched hydrocarbon group of 2 to 20 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

"Amino" is used herein to refer to the group —NR'R", where each of R' and R" is independently selected from the group consisting of hydrogen and optionally substituted alkyl, alkenyl, alkynyl, aryl, aralkyl, alkaryl and heterocyclic.

"Aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

"Aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain one aromatic ring or 2 to 4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. Typically the heteroaryl will contain 1-2 heteroatoms and 3-19 carbon atoms. Unless otherwise indicated, the terms "aryl" and "aromatic" includes heteroaromatic, substituted aromatic, and substituted heteroaromatic species.

"Aryldiketonate" refers to an aryl group, as defined herein, having two ketone carbonyl groups.

"Aryloxy" as used herein refers to an aryl group bound through a single, terminal ether linkage. An "aryloxy" group may be represented as —O-aryl, where aryl is as defined herein.

"Arylsulfonato" refers to the group the group —S(O)$_3$-aryl, where aryl is as defined herein.

"Carboxy" refers to the group —COOH.

"Carboxylato" is intended to mean the group —COO⁻.

The term "cyclic group" is intended to refer to any aliphatic or aromatic structure, and may contain substituents and/or heteroatoms. Typically although not necessarily a cyclic group is a 4-2 membered ring, preferably a 5- to 8-membered ring.

"Functional groups" (also referred to as "Fn") refer to groups such as halo, phosphonato, phosphoryl, phosphanyl, phosphino, sulfonato, sulfinyl, $C_{1-20}$ alkylsulfanyl, $C_{5-20}$ arylsulfanyl, $C_{1-20}$ alkylsulfonyl, $C_{5-20}$ arylsulfonyl, $C_{1-20}$ alkylsulfinyl, $C_{5-20}$ arylsulfinyl, sulfonamido, amino, amido, imino, nitro, nitroso, hydroxyl, $C_{1-20}$ alkoxy, $C_{2-20}$ alkenyloxy, $C_{2-20}$ alkynyloxy, $C_{5-20}$ aryloxy, $C_{1-20}$ carboxylato, $C_{2-20}$ alkylcarboxylato, $C_{5-20}$ arylcarboxylato, $C_{2-20}$ alkoxycarbonyl, $C_{5-20}$ aryloxycarbonyl, $C_{1-20}$ alkylsulfanyl, arylthio, mercapto, formyl, $C_{1-20}$ thioester, acyl, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge). Functional groups can also be substituted with one or more moieties selected from the group consisting of $C_{1-10}$ alkyl, $C_{1-10}$ alkoxy, aryl, hydroxyl, sulfhydryl, —(CO)—H, halo, as well as other functional groups. In addition, the term "functional group" is intended to include the functional group per se, as well as any linker group.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

"Hydrocarbyl" refers to univalent hydrocarbyl radicals containing about 1-30 carbon atoms, preferably about 1-20 carbon atoms, most preferably about 1-12 carbon atoms, including linear, branched, cyclic, saturated and unsaturated species, such as alkyl groups, alkenyl groups, alkynyl groups, alicyclic groups, aryl groups, aralkyl groups, alkaryl groups, and the like. The term "lower hydrocarbyl" intends a hydrocarbyl group of about 1-6 carbon atoms, and the term "hydrocarbylene" intends a divalent hydrocarbyl moiety containing about 1-30 carbon atoms, preferably about 1-20 carbon atoms, most preferably about 1-12 carbon atoms, including linear, branched, cyclic, saturated and unsaturated species. The term "lower hydrocarbylene" intends a hydrocarbylene group of about 1-6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Silyl" is intended to mean a silyl group (—SiH₃) or derivative thereof. The term silyl can thus be represented by the formula —SiR₃, where each R group is independently H, alkyl, cycloalkyl, cycloheteroalkyl, aryl or heteroaryl.

"Stereoselective" refers to a chemical reaction that preferentially results in one stereoisomer relative to a second stereoisomer, i.e., gives rise to a product in which the ratio of a desired stereoisomer to a less desired stereoisomer is greater than 1:1.

"Substituted" as in "substituted hydrocarbyl," "substituted alkyl," "substituted aryl," and the like, as alluded to in some of the aforementioned definitions, is meant that in the hydrocarbyl, alkyl, aryl, or other moiety at least one hydrogen atom bound to a carbon atom is replaced with one or more non-hydrogen substituents. Examples of such substituents include, without limitation functional groups ("Fn") as defined above; and hydrocarbyl moieties such as $C_{1-20}$ alkyl, $C_{2-20}$ alkenyl, $C_{2-20}$ alkynyl, $C_{5-20}$ aryl, $C_{5-30}$ aralkyl, and $C_{5-30}$ alkaryl. In addition, the aforementioned functional groups and hydrocarbyl moieties may, if a particular group permits, be further substituted with one or more additional functional groups or with one or more hydrocarbyl moieties such as those specifically enumerated above. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

In describing and claiming the present invention, the following abbreviations will be used in accordance with the definitions set out below.

| ABBREVIATIONS | |
|---|---|
| Ar | Aryl |
| ArBr | Bromoaryl |
| BINAP | 2,2'-bis(diphenylphosphino)-1,1'-binaphthyl |
| HC(OEt)₃ | triethyl orthoformate |
| NaO t-Bu | sodium tert-butoxide |
| o-Me | ortho-methyl |
| o-i-Pr | ortho-isopropyl |
| Pd(OAc)₂ | palladium acetate |

| ABBREVIATIONS | |
|---|---|
| Ph | Phenyl |
| PCy$_3$ | tricyclohexylphosphine |

The following description of the preferred embodiments and examples are provided by way of explanation and illustration. As such, they are not to be viewed as limiting the scope of the invention as defined by the claims. Additionally, when examples are given, they are intended to be exemplary only and not to be restrictive.

II. The Group 8 Transition Metal Carbene Complexes

The Group 8 transition metal carbene complexes of the invention have the formula (VI):

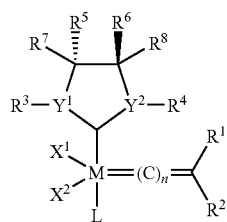

(VI)

M is a transition metal from Group 8 (iron, ruthenium, osmium) of the Periodic Table of the Elements, and serves as the transition metal center in the +2 oxidation state. Particularly suitable Group 8 transition metals are ruthenium or osmium. In a preferred embodiment, M is ruthenium.

$X^1$ and $X^2$ are independently selected from the group consisting of anionic ligands and polymers, or $X^1$ and $X^2$ may be taken together to form a cyclic group, typically although not necessarily a 5- to 8-membered ring. In preferred embodiments, $X^1$ and $X^2$ are independently selected from the group consisting of hydrogen, halo, $C_{1-20}$ alkyl, $C_{5-20}$ aryl, $C_{1-20}$ alkoxy, $C_{5-20}$ aryloxy, $C_{3-20}$ alkyldiketonate, $C_{5-20}$ aryldiketonate, $C_{2-20}$ alkoxycarbonyl, $C_{5-20}$ aryloxycarbonyl, $C_{2-20}$ acyl, $C_{1-20}$ alkylsulfonato, $C_{5-20}$ arylsulfonato, $C_{1-20}$ alkylsulfanyl, $C_{5-20}$ arylsulfanyl, $C_{1-20}$ alkylsulfinyl, and $C_{5-20}$ arylsulfinyl. Optionally, at least one of $X^1$ and $X^2$ are substituted with one or more moieties selected from the group consisting of $C_{1-10}$ alkyl, $C_{1-10}$ alkoxy, aryl, and halo, which may, in turn, with the exception of halo, be further substituted with one or more groups selected from halo, $C_{1-6}$ alkyl $C_{1-6}$ alkoxy, and phenyl. In more preferred embodiments, $X^1$ and $X^2$ are halo, benzoate, $C_{2-6}$ acyl, $C_{2-6}$ alkoxycarbonyl, $C_{1-6}$ alkyl, phenoxy, $C_{1-6}$ alkoxy, $C_{1-6}$ alkylsulfanyl, aryl, and $C_{1-6}$ alkylsulfonyl. In even more preferred embodiments, $X^1$ and $X^2$ are each halo, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each halo, preferably chloro.

The integer "n" can be from 0-5, and preferably will be from 0-3. In the most preferred embodiment, n is 0. Of the cumulenes, vinylidene (n=1) is preferred.

The complex may also comprise (i.e., be bound to) a solid support, such as a polymeric substrate, i.e., at least one of $X^1$ and $X^2$ can be a polymer. Such a polymer will also comprise an appropriate linker, by which attachment to the remainder of the complex may be effected. However, when the complex is bound to a solid support, in a preferred embodiment, the polymer is at one of the $R^3$ or $R^4$ positions or one of the $R^5$, $R^6$, $R^7$, and $R^8$ positions.

$R^1$ is selected from the group consisting of hydrogen, silyl, hydrocarbyl, substituted hydrocarbyl, heteroatom-containing hydrocarbyl, substituted heteroatom-containing hydrocarbyl, and carboxy. In a preferred embodiment, $R^1$ is hydrogen or $C_{5-20}$ aryl.

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group.

In a preferred embodiment, the $R^2$ substituent is selected from the group consisting of $C_{1-20}$ alkyl, $C_{2-20}$ alkenyl, and $C_{5-20}$ aryl. More preferably, $R^2$ is phenyl, vinyl, methyl, isopropyl, or t-butyl, optionally substituted with one or more moieties selected from the group consisting of $C_{1-6}$ alkyl, $C_{1-6}$ alkoxy, phenyl, and a functional group Fn. Still more preferably, $R^2$ is phenyl or vinyl substituted with one or more moieties selected from the group consisting of methyl, ethyl, chloro, bromo, iodo, fluoro, nitro, dimethylamino, methoxy, and phenyl. In the most preferred embodiments, the $R^2$ substituent is phenyl or $-C=C(CH_3)_2$. In another preferred embodiment, $R^1$ and $R^2$ are taken together to form a cyclic group, which may be aliphatic or aromatic, and may contain substituents and/or heteroatoms. Generally, such a cyclic group will contain 4 to 12, preferably 5 to 8, ring atoms.

$Y^1$ and $Y^2$ are heteroatoms independently selected from the group consisting of N, O, S, and P. In a preferred embodiment, $Y^1$ and $Y^2$ are the same. In another preferred embodiment $Y^1$ and $Y^2$ are nitrogen. The O and S heteroatoms are divalent, and therefore, it is understood that when either $Y^1$ or $Y^2$ is O or S, then $R^3$ or $R^4$, respectively, is absent.

$R^3$ and $R^4$ are independently selected from the group consisting of hydrogen, functional groups, hydrocarbyl, substituted hydrocarbyl, heteroatom-containing hydrocarbyl, substituted heteroatom-containing hydrocarbyl, and polymers. In one preferred embodiment, $R^3$ and $R^4$ are independently selected from the group consisting of $C_{5-20}$ aryl, hydrocarbyl-substituted $C_{5-20}$ aryl, and hydrocarbyl-substituted heteroaryl. In another preferred embodiment, at least one of $R^3$ and $R^4$ are functional groups connected directly to the N-heterocyclic carbene nitrogen, and are most preferably acyl. In another preferred embodiment at least one of $R^3$ and $R^4$, and more preferably, both $R^3$ and $R^4$, are alicyclic or aromatic structures having 1-5 rings, and optionally containing one or more heteroatoms and/or substituents. In another preferred embodiment, $R^3$ and $R^4$ are $C_{5-20}$ aryl, substituted $C_{5-20}$ aryl, heteroaryl, substituted heteroaryl, alicyclic, or substituted alicyclic, comprising about 1-5 rings. A preferred heteroaryl is a nitrogen-containing heterocycle such as pyrrole. When $R^3$ and $R^4$ are $C_{5-20}$ aryl, they typically although not necessarily have one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and each have the structure:

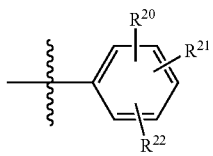

wherein $R^{20}$, $R^{21}$, and $R^{22}$ are independently selected from the group consisting of hydrogen, $C_{1-20}$ alkyl, substituted $C_{1-20}$ alkyl, perfluoronated $C_{1-20}$ alkyl (an alkyl chain that is saturated with fluorine atoms instead of hydrogen atoms), $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_5$-30 aralkyl, $C_{5-30}$ alkaryl, and halo.

In another embodiment, $R^{20}$, $R^{21}$, and $R^{22}$ are independently selected from the group consisting of hydrogen, methyl, ethyl, propyl, isopropyl, hydroxyl, halo, phenyl, and lower alkyl-substituted phenyl (e.g., dimethylphenyl). In yet another embodiment, $R^{20}$, $R^{21}$, and $R^{22}$ are each methyl.

In one preferred embodiment, the phenyl group shown above is substituted with a single ortho substituent, wherein the ortho substituent, in each of $R^3$ and $R^4$, is anti to the $R^5$ or $R^6$ substituent on the carbene, respectively. In a more preferred embodiment, the phenyl group is substituted with an ortho substituent and with an opposing meta substituent (such that the phenyl substituent is 2-substituted or 2,5-disubstituted). These particularly preferred configurations are illustrated in the following structure:

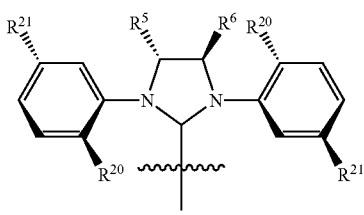

Such carbene ligands provide for complexes that are highly enantioselective metathesis catalysts.

In another embodiment, $R^3$ and $R^3$ are alicyclic and are comprised of a $C_{7-20}$, preferably a $C_{7-12}$, alicyclic structure, such as diisopinocamphenyl, as discussed in further detail infra.

The complex may also comprise a solid support, such as a polymeric substrate, i.e., at least one of $R^3$ and $R^4$ can be a polymer. Such a polymer will also comprise an appropriate linker, by which attachment to the remainder of the complex may be effected.

$R^5$, $R^6$, $R^7$, and $R^8$ are independently selected from the group consisting of polymers, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halide, and functional groups. In one embodiment, $R^5$, $R^6$, $R^7$, and $R^8$ are independently selected from the group consisting of hydrogen, $C_{1-10}$ alkyl (e.g., t-butyl), $C_{5-20}$ aryl, cyclohexyl, mesityl, and lower alkyl substituted phenyl. Exemplary $R^5$, $R^6$, $R^7$, and $R^8$ substituents are shown below:

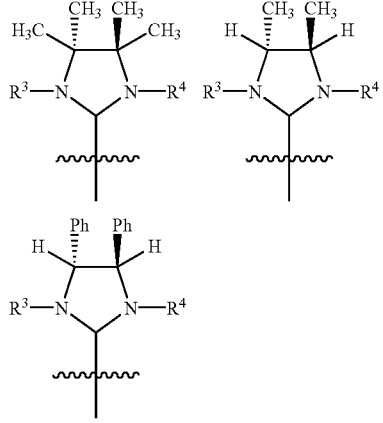

In addition, $R^5$, $R_6$, $R^7$, and $R^8$ may be linked together to form a substituted or unsubstituted, saturated or unsaturated ring structure, e.g., a $C_{4-12}$ alicyclic group or a $C_{5-6}$ aryl group, which may itself be substituted, e.g., with linked or fused alicyclic or aromatic groups, or with other substituents.

The complex may also comprise a solid support, such as a polymeric substrate, i.e., at least one of $R^5$, $R^6$, $R^7$, and $R^8$ can be a polymer. Such a polymer will also comprise an appropriate linker, by which attachment to the remainder of the complex may be effected.

L is a neutral electron donor ligand, and may or may not be linked to $R^2$, $X^1$, and/or $X^2$ through a spacer moiety. Examples of suitable L moieties include, without limitation, phosphine, sulfonated phosphine, phosphite, phosphinite, phosphonite, arsine, stibine, ether (including cyclic ethers), amino, amido, imino, sulfoxide, carboxy, nitrosyl, pyridyl, substituted pyridyl (e.g., halogenated pyridyl), imidazolyl, substituted imidazolyl (e.g., halogenated imidazolyl), pyrazinyl (e.g., substituted pyrazinyl), and thioether. In one preferred embodiment, L is a phosphine of the formula PR'R"R"', where R', R", and R"' are each independently $C_{1-10}$ alkyl (particularly primary alkyl, secondary alkyl or cycloalkyl), $C_{5-20}$ aryl or a heteroatom-containing functional group. In another embodiment, R', R", and R"' are the same, for example, —P(cyclohexyl)$_3$, —P(cyclopentyl)$_3$, —P(isopropyl)$_3$, —P(phenyl)$_3$. In yet another embodiment, L is —P(phenyl)$_2$(R) or —P(phenyl)(R)$_2$, where R is $C_{1-20}$ alkyl, typically lower alkyl. Also preferred are weaker ligands such as the nitrogen-containing heterocycles, which enhance catalytic activity presumably because of the requirement that the L ligand be lost for initiation to occur. Examples of complexes wherein L and $R^2$ are linked include the following:

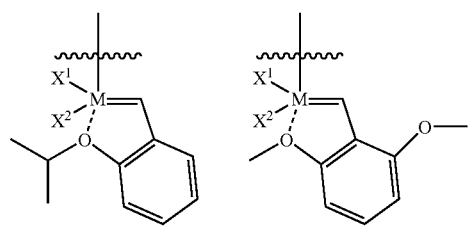

-continued

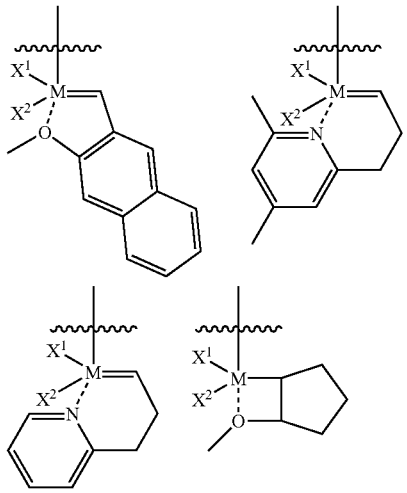

In addition, any two or more of $X^1$, $X^2$, L, $R^1$, $R^2$, $R^3$, $R^4$, $R^5$, $R^6$, $R^7$, and $R^8$ of the complex of formula (VI) can be taken together to form a chelating multidentate ligand, as described, for example, in Grubbs et al., U.S. Pat. No. 5,312, 940. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$ CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$— and —OC (CH$_3$)$_2$(CH$_3$)$_2$CO—. Preferred bidentate ligands are —P(Ph)$_2$ CH$_2$CH$_2$P(Ph)$_2$— and —P(CH$_3$)$_2$(CH$_2$)$_2$ P(CH$_3$)$_2$—. Tridentate ligands include, but are not limited to, (CH$_3$)$_2$ NCH$_2$CH$_2$P(Ph)CH$_2$CH$_2$N(CH$_3$)$_2$. Other preferred tridentate ligands are those in which any three of $X^1$, $X^2$, L, $R^1$, $R^2$, $R^3$, $R^4$, $R^5$, $R^6$, $R^7$, and $R^8$ (e.g., $X^1$, L, and any one of $R^3$, $R^4$, $R^5$, $R^6$, $R^7$, and $R^8$) are taken together to be cyclopentadienyl, indenyl or fluorenyl, each optionally substituted with $C_{2-20}$ alkenyl, $C_{2-20}$ alkynyl, $C_{1-20}$ alkyl, $C_{5-20}$ aryl, $C_{1-20}$ alkoxy, $C_{1-20}$ alkenyloxy, $C_{2-20}$ alkynyloxy, $C_{5-20}$ aryloxy, $C_{2-20}$ alkoxycarbonyl, $C_{1-20}$ alkylsulfanyl, $C_{1-20}$ alkylsulfonyl, or $C_{1-20}$ alkylsulfinyl, each of which may be further substituted with $C_{1-6}$ alkyl, halo, $C_{1-6}$ alkoxy or with a phenyl group optionally substituted with halo, $C_{1-6}$ alkyl or $C_{1-6}$ alkoxy. More preferably, in compounds of this type, $X^1$, L, and any one of $R^3$, $R^4$, $R^5$, $R^6$, $R^7$, and $R^8$ are taken together to be cyclopentadienyl or indenyl, each optionally substituted with vinyl, $C_{1-10}$ alkyl, $C_{5-20}$ aryl, $C_{1-10}$ carboxylato, $C_{2-10}$ alkoxycarbonyl, $C_{1-10}$ alkoxy, $C_{5-20}$ aryloxy, each optionally substituted with $C_{1-6}$ alkyl, halo, $C_{1-6}$ alkoxy or with a phenyl group optionally substituted with halo, $C_{1-6}$ alkyl or $C_{1-6}$ alkoxy. Most preferably, $X^1$, L, and any one of $R^3$, $R^4$, $R^5$, $R^6$, $R^7$, and $R^8$ may be taken together to be cyclopentadienyl, optionally substituted with vinyl, hydrogen, Me or Ph. Tetradentate ligands include, but are not limited to O$_2$C(CH$_2$)$_2$P (Ph)(CH$_2$)$_2$P(Ph)(CH$_2$)$_2$CO$_2$, phthalocyanines, and porphyrins.

The invention also encompasses a hexacoordinate complex where the Group 8 transition metal carbene complex of formula (VI) further comprises a second neutral electron donor ligand (L') attached to the Group 8 transition metal (M).

Catalysts formed with the ligands of the invention where $R^3$ and $R^4$ are each biphenylyl or substituted biphenylyl, are exemplified by the complex containing the 2,4,2',6'-tetramethylbiphenylyl-(i.e., 2,6-dimethyl-3-(2',6'-dimethylphenyl) phenyl-substituted ligand shown below:

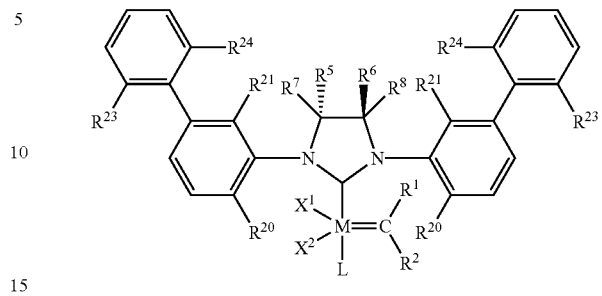

wherein $R^{20}$, $R^{21}$, $R^{23}$ and $R^{24}$ are independently selected from the group consisting of hydrogen, $C_{1-20}$ alkyl, substituted $C_{1-20}$ alkyl, perfluoronated $C_{1-20}$ alkyl, $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl, $C_{5-30}$ alkaryl, and halo.

Catalysts formed with the ligands of the invention where $R^3$ and $R^4$ are alicyclic, such diisopinocamphenyl, are exemplified by the complex containing the diisopinocamphenyl-substituted ligand shown below:

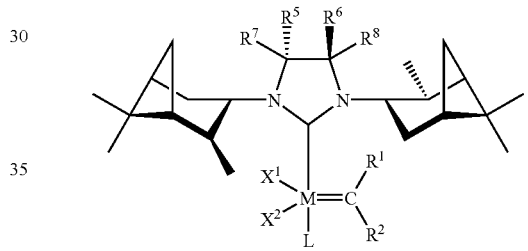

Ligands containing bulky, electron-donating groups such as those illustrated in the catalyst complexes above, provide for very highly active olefin metathesis catalysts. Such catalysts are thus suitable to catalyze reactions for which other, less active catalysts are ineffective, and are also useful in enhancing the stereoselectivity of a catalyzed cross-metathesis reaction.

Another example of a preferred catalyst useful in conjunction with the present methods is the ruthenium carbene complex of the formula (VII):

(VII)

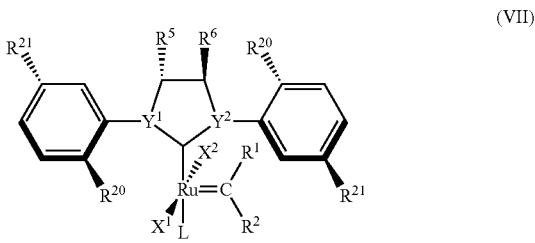

$X^1$ and $X^2$ are independently selected from the group consisting of anionic ligands and polymers, or $X^1$ and $X^2$ may be taken together to form a cyclic group. Preferred $X^1$ and $X^2$ groups are as identified above for formula (VI). $X^1$ and $X^2$ are most preferably halo.

$R^1$ is selected from the group consisting of hydrogen, silyl, hydrocarbyl, substituted hydrocarbyl, heteroatom-containing hydrocarbyl, substituted heteroatom-containing hydrocarbyl, and carboxyl. Preferred $R^1$ groups are as identified above for formula (VI). $R^1$ is most preferably hydrogen.

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group. Preferred $R^2$ groups are as identified above for formula (VI). $R^2$ is preferably $C_{5-20}$ aryl, most preferably phenyl.

$Y^1$ and $Y^2$ are heteroatoms independently selected from the group consisting of N, O, S, and P. Preferred $Y^1$ and $Y^2$ groups are as identified above for formula (VI). $Y^1$ and $Y^2$ are preferably the same, and most preferably nitrogen. As noted above, the O and S heteroatoms are divalent, and therefore, it is understood that when either $Y^1$ or $Y^2$ is O or S, then the appended aryl group is absent.

$R^5$ and $R^6$ are independently selected from the group consisting of polymers, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups. Preferred $R^5$ and $R^6$ groups are as identified above for formula (VI). $R^5$ and $R^6$ are most preferably $C_{5-20}$ aryl groups.

$R^{20}$ and $R^{21}$ are independently selected from the group consisting of hydrogen, $C_{1-20}$ alkyl, substituted $C_{1-20}$ alkyl, perfluoronated $C_{1-20}$ alkyl, $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl, $C_{5-30}$ alkaryl, and halo. The $R^{20}$ and $R^{21}$ are preferably in the anti-position relative to $R^5$ and $R^6$. In one embodiment, $R^{20}$ is an alkyl, and $R^{21}$ is hydrogen. In another preferred embodiment, $R^{20}$ and $R^{21}$ are alkyl groups.

L is a neutral electron donor ligand. Preferred L groups are as identified above for formula (VI). In one preferred embodiment, L is a phosphine having the formula PR'R"R''', where R', R", and R''' are each independently selected from the group consisting of $C_{1-10}$ alkyl and $C_{5-20}$ aryl. In a most preferred embodiment, L is selected from the group consisting of —P(cyclohexyl)$_3$, —P(cyclopentyl)$_3$, —P(isopropyl)$_3$, —P(phenyl)$_3$, —P(Phenyl)$_2$(R) and —P(phenyl)(R)$_2$, where R is alkyl.

III. Synthesis of The Group 8 Transition Metal Carbene Complexes

Synthesis of the enatiomerically pure complexes of the invention begins with a compound such as a commercially available 1,2-diamine (1) such as (1R,2R)-1,2-diaminocyclohexane or (1R,2R)-diphenylethylenediamine, or similar diamines that are readily synthesized, such as di-t-butylethylenediamine, diadamantylethylenediamine, dimesitylethylenediamine, and so forth. To the nitrogen atoms of this diamine are appended either alkyl or aryl groups through standard amination chemistry (e.g., using known N-alkylation procedures, for introduction of alkyl groups, or known amino dehalogenation chemistry, for introduction of aryl groups), to yield the desired product (3). For example, an N-aryl substituent can be introduced by reaction with an aryl halide through standard Pd-coupling reactions (Wolfe et al., *J. Org. Chem.* 65:1144-1157(2000)).

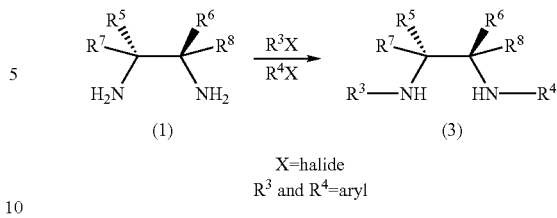

X=halide
$R^3$ and $R^4$=aryl

Synthesis of compounds (3) where $R^3$ and $R^4$ are alkyl groups, can be readily accomplished by an imine condensation as shown below, or through standard N-alkylation chemistry noted above.

Alternatively, an aldehyde or ketone can be condensed with the dianine and reduced in order to yield the desired product:

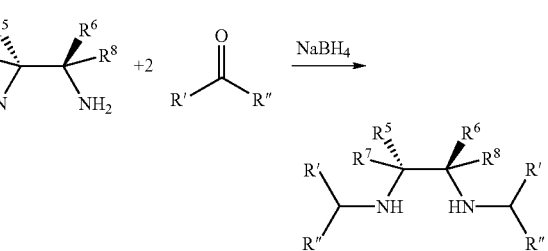

The resulting secondary amine is then condensed with a compound such as CH(Lg)$_3$ wherein Lg is a substituent displaceable by a nucleophile (e.g., triethyl orthoformate), and a salt having the formula $X^+Y^-$, such as an ammonium salt (e.g., ammonium tetrafluoroborate) to produce the corresponding imidazolium tetrafluoroborate salt (4) (Saba et al., *Tetrahedron Lett.* 32:5031-5034 (1991)):

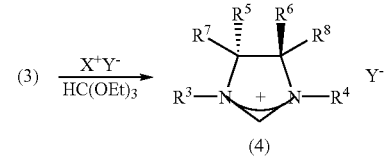

The salt (4) is then treated with a strong base such as sodium or potassium tert-butoxide or hexafluoro-tert-butoxide, e.g., potassium hexafluoro-tert-butoxide, followed by addition of $(L)_2X^1X^2M$=$CR^1R^2$, for example, $(PCy_3)_2(Cl)_2Ru$=CHPh, wherein the carbine displaces a single L group to generate the desired chiral complex (VI) in good yield:

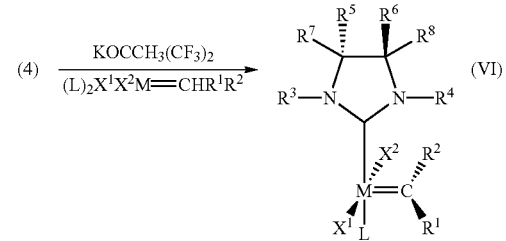

IV. Catalysis of Enantioselective Organic Transformations

The chiral Group 8 transition metal carbene complexes of Formula (VI) find particular utility as catalysts in effecting a host of enantioselective organic transformations. In particular, these complexes can be used to control the enantioselectivity of an olefin metathesis reaction by catalyzing the reaction with a chiral Group 8 transition metal carbene complex of the invention. In addition, these complexes can be treated with MX reagents, where M is an alkali metal and X can be any negatively charged counterion (e.g., Br⁻ or I⁻) in order to effect higher relative rates of enantioselectivity. For example, reaction of the neutral complex (VI) with lithium bromide or sodium iodide generates the bromide and iodide analogs of the complex, resulting in catalysts that exhibit enhanced enantioselectivity relative to the chloro counterpart (reaction with MX reagents should lead to exchange of the chloride groups for X groups without any change in charge).

Examples of olefin metathesis reactions that can benefit from the catalyst of the invention are set forth below. It is understood that the starting materials are representative of the "core" structure and that any compound comprising these core structures can also be used in the reactions.

Enantioselective Desymmetrization of Achiral and Meso Trienes

A meso-triene or achiral triene can undergo asymmetric ring-closing metathesis to afford optically-enriched substituted cyclic or heterocyclic olefins in a reaction catalyzed by the complex of formula (VI):

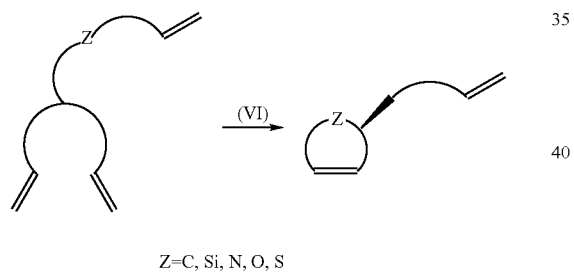

Z=C, Si, N, O, S

Examples of such desymmetrization reactions can be found in Example 5 and in Example 9.

Enantioselective Desymmetrization of Achiral and Meso Dienes

It is also expected that the catalysts of the invention will find utility in the desymmetrization reactions of achiral and meso dienes, in reactions catalyzed by the complex of formula (VI):

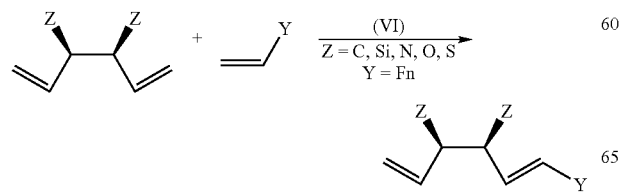

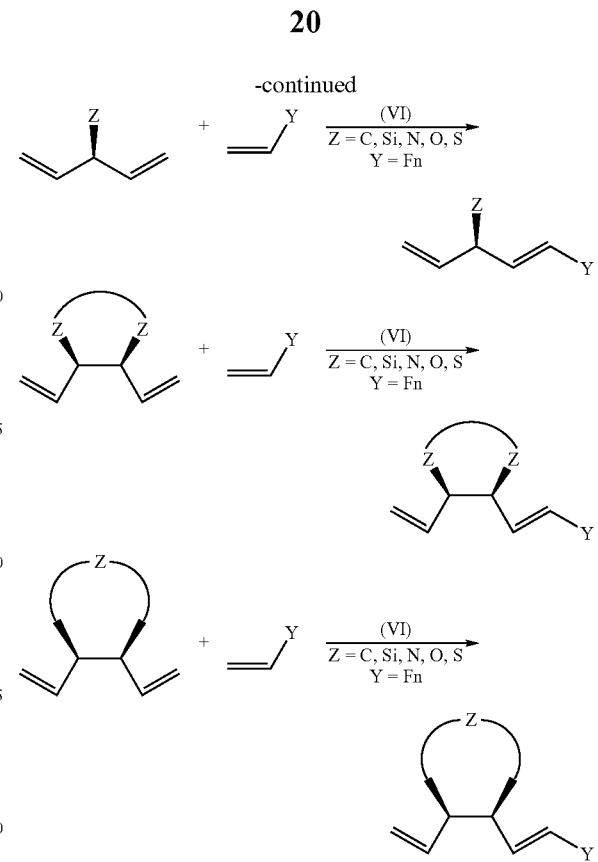

For example, the use of compounds such as 2,3-diol-1,4-diene derivatives, 2,4-diol-1,5-diene derivatives, and 3-ol-1,3-diene derivatives are expected to provide products possessing chiral hydroxyl stereocenters which are highly sought after functional groups in organic synthesis:

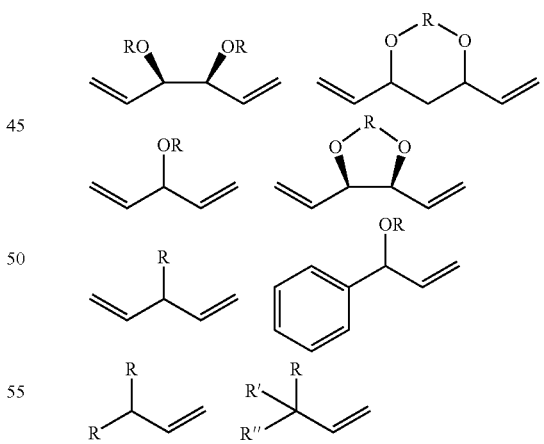

Enantioselective Ring-Opening/Ring-Closing Metathesis

The complex of formula (VI) may be used to treat a cyclic olefin substituted with two terminal olefin groups, to effect an enantioselective ring-opening/ring-closing metathesis reaction and thereby provide an optically enriched cyclic olefin:

Enantioselective Ring-Opening/Cross Metathesis

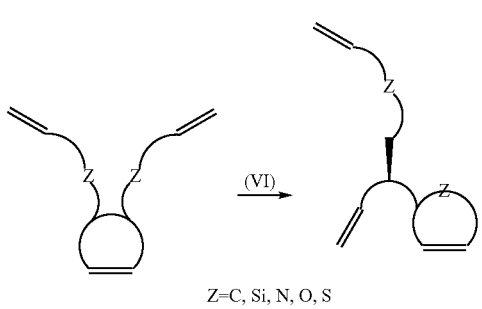

Z=C, Si, N, O, S

The complex of formula (VI) can effect the ring-opening/cross metathesis between a cyclic and an acyclic olefin to afford an optically enriched product:

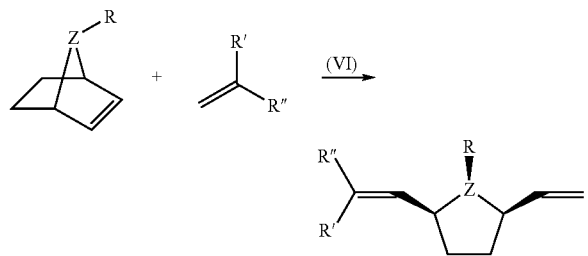

Z = C, Si, N, O, S; R, R', R" = alkyl, aryl

Kinetic Resolution Of Racemic Mixtures of Chiral Olefins

The complex of formula (VI) can effect a kinetic resolution via the enantioselective cross metathesis of a racemic mixture of a chiral olefin with another olefinic reactant, to afford an optically active product and starting material:

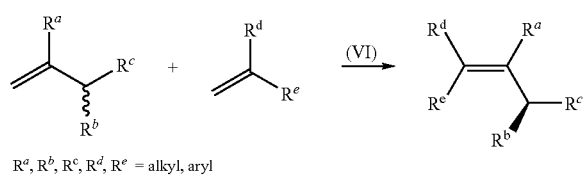

$R^a, R^b, R^c, R^d, R^e$ = alkyl, aryl

The complex of formula (VI) can also be used to effect kinetic resolutions through the enantioselective ring-closing of a racemic diene, affording partial conversion to an optically enriched sample of the starting material and an optically enriched cyclic olefin product:

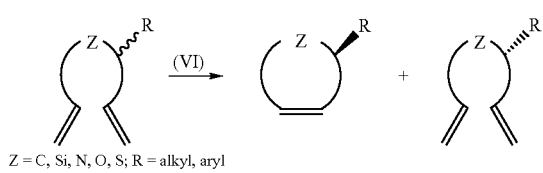

Z = C, Si, N, O, S; R = alkyl, aryl

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Accordingly, the scope of the invention should therefore be determined with reference to the appended claims, along with the full range of equivalents to which those claims are entitled.

EXAMPLES

General Procedures, Materials and Methods

When specified, manipulation of organometallic compounds was performed using standard Schlenk techniques under an atmosphere of dry argon or in a nitrogen-filled Vacuum Atmospheres drybox ($O_2$<2 ppm). NMR spectra were recorded on a Varian Inova (499.85 MHz for $^1H$; 202.34 MHz for $^{31}P$; 125.69 MHz for $^{13}C$) or a Varian Mercury 300 (299.817 for $^1H$; 121.39 MHz for $^{31}P$; 74.45 MHz for $^{13}C$). $^{31}P$ NMR spectra were referenced using $H_3PO_4$ ($\delta$=0 ppm) as an external standard.

Toluene, dichloromethane, tetrahydrofuran, and benzene were dried by passage through solvent purification columns. Silica gel was obtained from TSI.

The starting materials, (1R,2R)-1,2-diaminocyclohexane (1) and (1R,2R)-diphenylethylenediamine (2) (Wolfe et al., Acc. Chem. Res. 31:805-818 (1998) and Yang et al., J. Organomet. Chem. 576:125-146 (1999)), as well as the reagents used in the synthesis are either commercially available or can be synthesized by methods that are well known in the art.

The following scheme provides for the synthesis of those compounds where $R^1$ and $R^2$ are taken together to form a phenyl; $R^3$ and $R^4$ are aryl; $R^7$ and $R^8$ are hydrogen; $X^1$ and $X^2$ are chloro; L is $PCy_3$; and M is ruthenium. However, it is understood that these schemes can be readily modified to introduce other $R^1$, $R^2$, $R^3$, $R^4$, $R^7$ and $R^8$ substituents, $X^1$ and $X^2$ substituents, as well as other L and M groups.

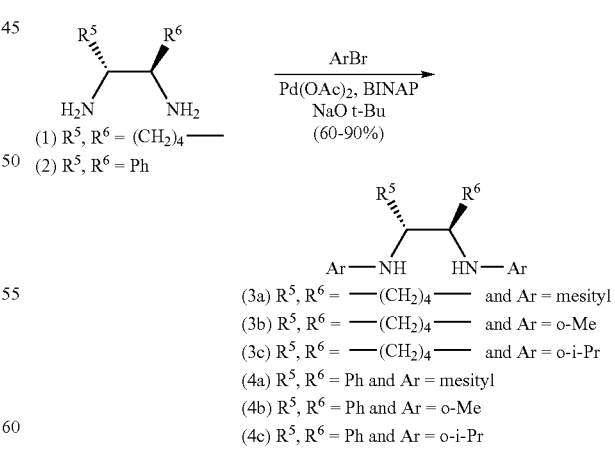

(1) $R^5, R^6$ = $(CH_2)_4$—
(2) $R^5, R^6$ = Ph (3a) $R^5, R^6$ = —$(CH_2)_4$— and Ar = mesityl
(3b) $R^5, R^6$ = —$(CH_2)_4$— and Ar = o-Me
(3c) $R^5, R^6$ = —$(CH_2)_4$— and Ar = o-i-Pr
(4a) $R^5, R^6$ = Ph and Ar = mesityl
(4b) $R^5, R^6$ = Ph and Ar = o-Me
(4c) $R^5, R^6$ = Ph and Ar = o-i-Pr The resulting diamines (3a, 3b, 3c, 4a, 4b, 4c) are then condensed with triethyl orthoformate and ammonium tetrafluoroborate to produce the corresponding imidazolium tetrafluoroborate salts (5a, 5b, 5c, 6a, 6b, 6c) (Saba et al., Tetrahedron Lett. 32:5031-5034 (1991)):

(3a)
(3b)
(3c)
(4a)
(4b)
(4c)

$\xrightarrow{\text{NH}_4\text{BF}_4}$
HC(OEt)$_3$
(80-90%)

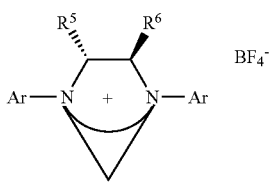

(5a) $R^5, R^6 =$ —(CH$_2$)$_4$— and Ar = mesityl
(5b) $R^5, R^6 =$ —(CH$_2$)$_4$— and Ar = o-Me
(5c) $R^5, R^6 =$ —(CH$_2$)$_4$— and Ar = o-i-Pr
(6a) $R^5, R^6 =$ Ph and Ar = mesityl
(6b) $R^5, R^6 =$ Ph and Ar = o-Me
(6c) $R^5, R^6 =$ Ph and Ar = o-i-Pr These salts (5a, 5b, 5c, 6a, 6b, 6c) are then treated with potassium hexafluoro-tert-butoxide (note that if potassium t-butoxide is used, the yields of 7 and 8 are dramatically reduced and a t-butoxide adduct of ruthenium forms, Sanford et al., *Angew. Chem., Int. Ed.* 39:3451-3453 (2000)), followed by (PCy$_3$)$_2$(Cl)$_2$Ru=CHPh to displace a single PCy$_3$ and generate the desired chiral complexes (7a, 7b, 7c, 8a, 8b, 8c) in good yield:

(5a)
(5b)
(5c)
(6a)
(6b)
(6c)

$\xrightarrow[\text{(PCy}_3\text{)}_2\text{Cl}_2\text{Ru}=\text{CHPh}]{\text{KOCCH}_3\text{(CF}_3\text{)}_2}$
(50-80%)

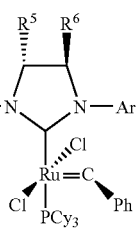

(7a) $R^5, R^6 =$ —(CH$_2$)$_4$— and Ar = mesityl
(7b) $R^5, R^6 =$ —(CH$_2$)$_4$— and Ar = o-Me
(7c) $R^5, R^6 =$ —(CH$_2$)$_4$— and Ar = o-i-Pr
(8a) $R^5, R^6 =$ Ph and Ar = mesityl
(8b) $R^5, R^6 =$ Ph and Ar = o-Me
(8c) $R^5, R^6 =$ Ph and Ar = o-i-Pr Complexes (7a), (7b), (7c), (8a), (8b), and (8c) are air-stable solids and are easily purified on the bench top by column chromatography (Kingsbury et al., *J. Am. Chem. Soc.* 121:791-799 (1999)). The bromide and iodide analogues of these complexes are generated in situ by the addition of LiBr or NaI, respectively (Sanford et al., *J. Am. Chem. Soc.* 123: 6543-6554 (2001)).

Example 1

Representative Preparation of Diamine (4b)

Under inert atmosphere, Pd (OAc)$_2$ (0.016 g, 0.071 mmol), BINAP (0.088 g, 0.14 mmol), and NaO t-Bu (0.410 g, 4.26 mmol) were added to toluene (25 mL) and stirred for 20 min. (R,R)-diphenylethylenediamine (0.300 g, 1.42 mmol) (2) and ArBr (0.510 g, 2.98 mmol) were then added and the solution was heated to 100° C. for 16 hours. The solution was then cooled to ambient temperature, diluted with hexanes (75 mL), and filtered through a plug of silica. The silica was washed with methylene chloride to elute the product. The volatiles were removed in vacuo to yield diamine (4b) as a white solid (0.52 g, 93%).

mp 49-51° C. $[\alpha]^{22}_D$ +18.6° (c 0.5, CH$_2$Cl$_2$). $^1$H NMR (300 MHz, CDCl$_3$): δ 2.15 (s, 6H), 4.73 (s, 2H), 6.33 (bs, 2H), 6.62 (t, J=7.5 Hz, 2H), 6.91 (t, J=7.8 Hz, 2H), 7.01 (d, J=7.2 Hz, 2H), 7.25 (m, 10H). $^{13}$C NMR (125 MHz, CDCl$_3$): δ 17.7, 63.9, 111.8, 117.6, 122.9, 126.8, 127.0, 127.6, 128.5, 129.9, 139.7, 144.7. FAB HRMS [M+H] m/z: found 393.2319, calculated (C$_{28}$H$_{29}$N$_2$) 393.2331. Anal. calculated for C$_{28}$H$_{28}$N$_2$: C, 85.67; H, 7.19; N, 7.14. Found C, 85.52; H, 7.31; N, 7.03.

Diamine (4a)

Diamine (4a) was synthesized in an analogous manner to provide a yield of 80%.

mp 65-67° C. $[\alpha]^{22}_D$ −7.5° (c 0.5, CH$_2$Cl$_2$). $^1$H NMR (300 MHz, CDCl$_3$): δ 2.10 (s, 12H), 2.15 (s, 6H), 3.99 (s, 2H), 4.78 (s, 2H), 6.69 (s, 4H), 6.84 (m, 4H), 7.12 (m, 6H). $^{13}$C NMR (125 MHz, CDCl$_3$): δ 19.5, 20.5, 66.5, 127.0, 127.6, 128.3, 128.6, 129.6, 130.3, 140.5, 141.5. FAB HRMS [M+H] m/z: found 449.2969, calculated (C$_{32}$H$_{37}$N$_2$) 449.2957.

Diamine (4c)

Diamine (4c) was synthesized in an analogous manner to provide a yield of 70%.

mp 86-88° C. $[\alpha]^{22}_D$ +16.90 (c 0.5, CH$_2$Cl$_2$). $^1$H NMR (300 MHz, CDCl$_3$): δ 1.15 (d, J=6.9 Hz, 6H), 1.30 (d, J=6.9 Hz, 6H), 2.89 (s, J=6.9 Hz, 2H), 4.74 (s, 2H), 6.29 (d, J=8.1 Hz, 2H), 6.69 (t, J=7.2 Hz, 2H), 6.88 (d, J=7.2 Hz, 2H), 7.11 (d, J=7.5 Hz, 2H), 7.2-7.3 (m, 10H). $^{13}$C NMR (125 MHz, CDCl$_3$): δ 22.5, 23.4, 27.5, 63.9, 112.4, 117.8, 124.7, 126.3, 126.9, 127.6, 128.6, 133.0, 139.9, 143.3. FAB HRMS [M+H] m/z: found 449.2962, calculated (C$_{32}$H$_{37}$N$_2$) 449.2957.

Diamine (3a)

Diamine (3a) was synthesized in an analogous manner to provide a yield of 53%.

mp 122° C. $[\alpha]^{22}_D$ +37° (c=1.05, CH$_2$Cl$_2$). $^1$H NMR (300 MHz, CDCl$_3$): δ 1.17 (br, 4H), 1.62 (br, 2H), 1.83 (br, 2H), 2.24 (s, 6H), 2.31 (s, 12H), 3.06 (br, 2H), 3.40 (br, 2H), 6.82 (s, 4H). $^{13}$C NMR (125 MHz, CDCl$_3$): δ 19.34, 20.72, 25.03, 32.87, 62.26, 129.61, 130.85, 131.27, 142.13. IR (KBr, cm$^{-1}$) 584.3, 726.3, 753.2, 852.4, 1222.6, 1448.5, 1480.0, 2852.7, 2925.9, 3320.3, 3449.4. FAB HRMS [M+] m/z: found 350.2718, calculated (C$_{24}$H$_{34}$N$_2$) 350.2722.

Diamine (3b)

Diamine (3b) was synthesized in an analogous manner to provide a yield of 67%.

mp 84° C. $[\alpha]^{22}_D$ =−27° (c=0.94, CH$_2$Cl$_2$). $^1$H NMR (300 MHz, CDCl$_3$): δ 1.2-1.6 (br m, 4H); 1.81 (br, 2H); 2.01(s, 6H); 2.38 (d, J=12.3 Hz, 2H); 3.35 (br, 2H); 3.7 (br, 2H); 6.68 (t, J=7.2 Hz, 1H); 6.75 (d, J=6.6 Hz, 1H); 7.05 (d, J=7.2 Hz, 1H); 7.14 (t, J=8.1 Hz, 1H). $^{13}$C NMR (125 MHz, CDCl$_3$): δ 17.79, 24.93, 32.99, 57.85, 110.52, 117.27, 122.98, 127.21, 130.57, 145.99. IR (KBr, cm$^{-1}$) 745.3, 982.2, 1039.4, 1050.8, 1115.0, 1141.2, 1257.5, 1310.0, 1500.3, 1605.0, 2848.7, 2949.8, 3394.0. FAB HRMS [M+] m/z: found 294.2091, calculated (C$_{20}$H$_{26}$N$_2$) 294.2096. Anal. Calculated for C$_{20}$H$_{26}$N$_2$: C, 81.59; H, 8.90; N, 9.51. Found C, 81.71; H, 8.93; N, 9.38.

Diamine (3c)

Diamine (3c) was synthesized in an analogous manner to provide a yield of 70%.

$[\alpha]^{22}_D$=−30.0° (c=0.59, $CH_2Cl_2$). $^1H$ NMR (300 MHz, $CDCl_3$): ☐ 1.10 (d, J=6.9 Hz, 6H); 1.19 (d, J=6.6 Hz, 6H); 1.2-1.5 (br m, 4H); 1.81 (br m, 2H); 2.40 (d, J=12.9 Hz, 2H); 2.72 (m, J=6.6 Hz, 2H); 3.36 (d, J=8.1 Hz, 2 H); 3.89 (br s, 2H); 6.76 (br s, 4H); 7.13 (br m, 4H). $^{13}C$ NMR (125 MHz, $CDCl_3$): δ 22.43, 22.56, 24.95, 27.12, 32.83, 57.84, 111.25, 117.62, 125.42, 126.75, 133.28, 144.53. IR (neat, $cm^{-1}$) 745.3, 1038.7, 1162.0, 1254.4, 1302.1, 1359.6, 1453.8, 1513.7, 1583.0, 1602.5, 2860.1, 2959.6, 3036.4, 3064.4, 3424.7. FAB HRMS [M+] m/z: found 350.2714, calculated ($C_{24}H_{34}N_2$) 350.2722.

Example 2

Representative Preparation of Salt (6b)

Diamine (4b) (0.290 g, 0.74 mmol), ammonium tetrafluoroborate (0.093 g, 0.89 mmol), and $HC(OEt)_3$ (1 mL) were heated to 120° C. for 5 hours. The solution was then allowed to cool to ambient temperature, and the product was precipitated and washed 3 times with diethyl ether (3 X 10 mL). The solids were dissolved in methylene chloride and filtered, and the volatiles were removed in vacuo to yield (6b) as an off-white solid (0.360 g, 99%).

mp 188-191° C. $[\alpha]^{22}_D$ +32.2° (c 0.5, $CH_2Cl_2$). $^1H$ NMR (300 MHz, $CDCl_3$): δ 2.45 (s, 6H), 5.78 (s, 2H), 7.17 (m, 6H), 7.39 (m, 12H), 8.32 (s, 1H). $^{13}C$ NMR (125 MHz, $CDCl_3$): δ 18.5, 76.1, 127.6, 127.7, 128.0, 129.6, 130.0, 130.2, 131.6, 132.5, 133.3, 133.4, 157.3. FAB HRMS [M+(−$BF_4$)] m/z: found 403.2159, calculated ($C_{29}H_{27}N_2$) 403.2174.

Salt (6a)

Salt (6a) was synthesized in an analogous manner to provide a yield of 70%.

mp 127-130° C. $[\alpha]^{22}_D$+23.7° (c 0.5, $CH_2Cl_2$). $^1H$ NMR (300 MHz, $CDCl_3$): δ 1.93 (s, 6H), 2.23 (s, 6H), 2.67 (s, 6H), 5.98 (s, 2H), 6.75 (s, 2H), 6.98 (s, 2H), 7.37 (m, 10H), 7.39, 8.65 (s, 1H). $^{13}C$ NMR (125 MHz, $CDCl_3$): δ 18.3, 19.1, 21.1, 72.9, 128.5, 128.8, 129.4, 130.1, 130.7 (2), 131.5, 134.0, 136.1, 140.3, 158.2. FAB HRMS [M+(−BF4)] m/z: found 459.2812, calculated ($C_{33}H_{35}N_2$) 459.2800.

Salt (6c)

Salt (6c) was synthesized in an analogous manner to provide a yield of 73%.

mp 115-118° C. $[\alpha]^{22}_D$ +27.8° (c 0.5, $CH_2Cl_2$). $^1H$ NMR (300 MHz, $CDCl_3$): δ 1.18 (d, J=6.6 Hz, 6H), 1.33 (d, J=7.2 Hz, 6H), 3.13 (sept, J=6.9 Hz, 2H), 5.79 (s, 2H), 7.2-7.5 (m, 16H), 7.58 (d, J=8.1 Hz, 2H), 8.25 (s, 1H). $^{13}C$ NMR (125 MHz, $CDCl_3$): δ 24.1, 24.7, 28.7, 77.1, 126.7, 127.7, 128.3, 128.5, 129.6, 130.3 (2),130.7, 132.7, 144.4, 157.3. FAB HRMS [M+(−BF4)] m/z: found 459.2800, calculated ($C_{33}H_{35}N_2$) 459.2800.

Salt (5a)

Salt (5a) was synthesized in an analogous manner to provide a yield of 99%.

mp 187° C. $[\alpha]^{22}_D$ +29.7° (c 1.04, $CH_2Cl_2$). $^1H$ NMR (300 MHz, $CD_2Cl_2$): δ 1.33-1.44 (br m, 2H); 1.66-1.84 (br m, 2H); 1.94-2.10 (br m, 4H); 2.30 (s, 6H); 2.35 (s, 6H); 2.37 (s, 6H); 4.10 (br m, 2H); 7.04 (s, 2H); 7.08 (s, 2H); 8.24 (s, 1H). $^{13}C$ NMR (125 MHz, $CD_2Cl_2$): δ 18.17, 18.85, 21.33, 24.20, 27.94, 71.50, 129.42, 130.56, 130.71, 135.17, 136.68, 141.45, 161.20. IR (KBr, $cm^{-1}$): 519.2, 578.2, 742.5, 848.0, 939.3, 1063.6, 1168.8, 1235.3, 1251.7, 1272.6, 1388.4, 1451.6, 1482.3, 1578.8, 1613.5, 2951.9, 3049.1, 3422.9. FAB HRMS [M+(−BF4)] m/z: found 361.2641, calculated ($C_{25}H_{33}N_2$) 361.2644.

Salt (5b)

Salt (5b) was synthesized in an analogous manner to provide a yield of 90%.

mp 213° C. $[\alpha]^{22}_D$ +33.5° (c 0.97, $CH_2Cl_2$). $^1H$ NMR (300 MHz, $CD_2Cl_2$): δ 1.41 (br m, 2H); 1.79 (br m, 2H); 1.99 (br m, 2H); 2.12 (br d, J=11.1 Hz, 2H); 2.41 (s, 6H); 4.21 (br m, 2H); 7.42 (m, 8H); 8.16 (s, 1H). $^{13}C$ NMR(125 MHz, $CD_2Cl_2$): δ 18.11, 24.15, 27.87, 71.77, 127.36, 128.29, 130.92, 132.42, 133.39, 134.99, 159.72. IR (KBr, $cm^{-1}$): 524.0, 766.7, 1066.6, 1162.5, 1256.0, 1303.0, 1450.2, 1496.6, 1573.6, 1595.4, 2874.5, 2961.9, 3072.2, 3441.3. FAB HRMS [M+(−BF4)] m/z: found 305.2018, calculated ($C_{21}H_{25}N_2$) 305.2018.

Salt (5c)

Salt (5c) was synthesized in an analogous manner to provide a yield of 93%.

mp 205° C. $[\alpha]^{22}_D$ +20.4° (c 1.0, $CH_2Cl_2$). $^1H$ NMR (300 MHz, $CD_2Cl_2$): δ 1.23-1.46 (br m, 16H); 1.92-2.18 (br m, 4H); 2.6-3.5 (br m, 2H); 3.7-4.6 (br m, 2H); 7.37-7.44 (br m, 3H); 7.44-7.60 (br m, 5H); 8.00 (s, 1H). $^{13}C$ NMR (125 MHz, $CD_2Cl_2$): spectrum is broad, 23.49, 24.10, 24.85, 27.72, 28.86, 72.38, 126.81, 127.86, 128.17, 129.86, 131.53, 146.22, 159.72. IR (KBr, $cm^{-1}$) 498.6, 557.1, 598.3, 768.5, 1050.1, 1162.6, 1248.1, 1449.2, 1491.5, 1574.2, 1596.6, 2870.2, 2965.9, 3066.8, 3422.8. FAB HRMS [M+(−BF4)] m/z: found 361.2647, calculated ($C_{25}H_{33}N_2$) 361.2644.

Example 3

Preparation of Complex (8b)

In a glove box, imidazolium salt (6b) (0.200 g, 0.408 mmol) and potassium hexafluoro-t-butoxide (0.108 g, 0.490 mmol) were dissolved in tetrahydrofuran (4 mL), added to a solution of bis(tricyclohexylphosphine)-benzylidene ruthenium dichloride (0.403 g, 0.490 mmol) in toluene (10 mL), and transferred to a Schlenk flask. The flask was removed from the glove box and heated to 50° C. under argon for 2 hours. The solution was cooled to ambient pentane temperature and the volatiles were removed in vacuo. The product was purified by column chromatography ($SiO_2$, 7:1 :$Et_2O$) to yield (8b) as a brown microcrystalline solid (0.300 g, 78%).

mp 142-144° C. $[\alpha]^{22}_D$ +6.0° (c 0.005, $CH_2Cl_2$). $^1H$ NMR (500 MHz, $CDCl_3$) exists as a mixture of atropisomers (3.2:1): δ 0.9-2.9 (m, $ArCH(CH_3)_2$+$PCy_3$), 5.01 (bs, $NCHPh$,), 5.17 bs, NCHPh), 6.5-7.6 (m, ArH), 8.15 (bs, o-ArH of benzylidene), 19.41 (s, Ru=CHPh), 19.46 (s, Ru=CHPh). $^{13}C$ NMR(125 MHz, C6D6): δ 221.0 (NCN), 297.3 (NCN Ru=CHPh). $^{31}P$ NMR (121 MHz, C6D6): δ 26.96. IR (KBr, $cm^{-1}$) 3059, 3030, 2925 (s), 2849 (s), 1493 (s), 1446 (s), 1419 (s), 762, 743, 721, 710. ES HRMS [M−Cl]+ m/z: found 909.3647, calculated ($C_{54}H_{65}ClN_2PRu$) 909.3647. Anal. calculated for $C_{54}H_{65}Cl_2N_2PRu$: C, 68.63; H, 6.93; N, 2.96. Found C, 69.19; H, 7.01; N, 3.03.

Complex (8a)

Complex (8a) was synthesized in an analogous manner to provide a yield of 78%.

mp 140-142° C. $[\alpha]^{22}_D$ −0.6° (c 0.005, $CH_2Cl_2$). $^1H$ NMR (500 MHz, $CD_2Cl_2$) exists as a mixture of atropisomers (1.1:1): δ 0.9-3.1 (broad multiplets, $ArCH(CH_3)_2+PCy_3$), 5.5-7.5 (broad multiplets, ArH), 9.0 (broad singlet), 19.10 (s, Ru=CHPh), 19.25 (s, Ru=CHPh). $^{13}C$ NMR (125 MHz, $C_6D_6$): δ 223.7 (bs, NCN), 295.6 (Ru=CHPh), 296.6 (Ru=CHPh). $^{31}P$ NMR (121 MHz, $C_6D_6$): δ 29.16. IR (KBr, $cm^{-1}$) 2924 (s), 2850 (s), 1446 (s), 1401, 1378, 1237 (s), 736, 697. ES HRMS [M−Cl]+ m/z: found 965.4232, calculated ($C_{58}H_{73}ClN_2PRu$) 965.4257. Anal. calculated for $C_{58}H_{73}Cl_2N_2PRu$: C, 69.58; H, 7.35; N, 2.80. Found C, 69.79; H, 7.61; N, 2.59.

Complex (8c)

Complex (8c) was synthesized in an analogous manner to provide a yield of 78% (0.300 g).

mp 150-155 ° C. $[\alpha]^{22}_D$ +21.0° (c 0.005, $CH_2Cl_2$). $^1H$ NMR (500 MHz, $CD_2Cl_2$) exists as a mixture of atropisomers (27:1): δ 0.9-1.9 (m, $ArCH(CH_3)_2+PCy_3$), 3.53 (m, ArCH $(CH_3)_2$), 3.76 (m, $ArCH(CH_3)_2$), 4.92 (d, J=4 Hz, NCHPh,), 5.23 (d, J=4 Hz, NCHPh), 6.6-7.6 (m, ArH), 8.59 (d, J=7 Hz), 19.25 (s, Ru=CHPh), 19.34 (s, Ru=CHPh). $^{13}C$ NMR (125 MHz, $C_6D_6$): δ 220.2 (d, J=75.6 Hz, NCN), 298.2 (NCN Ru=CHPh). $^{31}P$ NMR (121 MHz, $CD_2Cl_2$): δ 24.9. IR (KBr, $cm^{-1}$) 3060, 2926 (s), 2849 (s), 1489 (s), 1448 (s), 1417 (s), 758 (s), 702 (s). ES HRMS [M−Cl]+ m/z: found 965.4283, calculated ($C_{58}H_{73}ClN_2PRu$) 965.4257. Anal. calculated for $C_{58}H_{73}Cl_2N_2PRu$: C, 69.58; H, 7.35; N, 2.80. Found C, 70.27; H, 7.64; N, 2.61.

Complex (7a)

Complex (7a) was synthesized in an analogous manner to provide a yield of 80%.

$[\alpha]^{22}_D$=+100.5° (c=0.19, $CH_2Cl_2$). $^1H$ NMR (500 MHz, $CD_2Cl_2$ (27:1): δ 0.60-1.52 (br m, 34H); 1.53 (d, J=1 Hz, 6H); 1.62-1.80 (br m, 3H); 1.90 (s, 3H); 1.91-2.25 (br m, 4H); 2.30 (s, 3H); 2.33-2.78 (br m, 6H); 3.47-4 (br m, 2H); 5.77 (br s, 1H); 6.62-7.45 (br m, 7H); 8.97 (br s, 1H); 19.00 (s, 1H). $^{13}C$ NMR (125 MHz, $C_6D_6$): δ 225.52 (br, NCN); 294.07, 294.35 (Ru=CHPh). $^{31}P$ NMR (121 MHz, $CD_2Cl_2$): δ 30.02. IR (KBr, $cm^{-1}$) 687.0, 848.2, 897.6, 1135.8, 1257.7, 1360.0, 1384.5, 1445.4, 1480.1, 2850.8, 2925.1, 3437.8. ES HRMS [M−Cl]+ m/z: found, 867.4092, calculated ($C_{50}H_{71}ClN_2PRu$) 867.4098.

Complex (7b)

Complex (7b) was synthesized in an analogous manner to provide a yield of 73%.

$[\alpha]^{22}_D$=−68° (c=0.05, $CH_2Cl_2$). $^1H$ NMR (500 MHz, $CD_2Cl_2$) exists as a mixture of atropisomers: δ 0.72-2.29 (br m, 45 H); 2.49-2.78 (br m, 2H); 3.35-4.05 (br m, 2H); 5.92-8.33 (br m, 13 H); 18.93-19.03 (br m, 1H). $^{13}C$ NMR (125 MHz, $CD_2Cl_2$): δ 227.61 (d, J=73 Hz, NCN); 296.40 (br s, Ru=CHPh). $^{31}P$ NMR (121 MHz, $CD_2Cl_2$): δ 25.60, 27.95, 28.83. IR (KBr, $cm^{-1}$) 678.5, 721.7, 1147.4, 1261.9, 1446.2, 1491.8, 1636.6, 2849.6, 2925.7, 3447.9. ES HRMS [M−Cl]+ m/z: found 811.3456, calculated ($C_{46}H_{63}ClN_2PRu$) 811.3470.

Complex (7c)

Complex (7c) was synthesized in an analogous manner to provide a yield of 75%.

$[\alpha]^{22}_D$=−120° (c=0.05, $CH_2Cl_2$). $^1H$ NMR (500 MHz, $CD_2Cl_2$) exists as a mixture of atropisomers (4.9:1): δ 0.80-2.01 (br m, 53 H); 3.07-4.00 (br m, 4H); 6.04-8.48 (m, 13H); 19.04 (s, 0.83 H); 19.21 (s, 0.17 H). $^{13}C$ NMR (125 MHz, $CD_2Cl_2$): δ 274.00 (d, J=78 Hz, NCN); 298.51 (br s, Ru=CHPh). $^{31}P$ NMR (121 MHz, $CD_2Cl_2$): δ 23.85, 25.70, 29.65. IR (KBr, $cm^{-1}$) 678.1, 756.0, 848.6, 897.1, 1259.7, 1447.4, 1489.6, 1559.4, 1653.8, 2849.6, 2925.1, 3447.4. ES HRMS [M−Cl]+ m/z: found 867.4080, calculated ($C_{50}H_{71}ClN_2PRu$) 867.4098.

Example 4

Preparation of Bis(pyridine) Adduct (9)

Although crystals have not been forthcoming for complexes (8b) and (8c), crystallographic evidence of the conformation of the chiral NHC ligands has been obtained by conversion of complex (8b) to bis(pyridine) adduct (9) by the procedure described below. The crystal structure of complex (9) (not shown) indicated that the NHC ligand is approximately $C_2$-symmetric with the o-methyl group oriented anti to the phenyl substituent of the imidazole ring. Additionally, the phenyl group of the benzylidene is oriented anti to the o-methyl substituent of the proximal aryl ring. This anti-anti arrangement suggests that the stereochemistry of the phenyl substituents on the imidazole ring is effectively transferred to the metal center.

Pyridine (0.20 mL) was added to a solution of (8b) (0.050 g, 0.053 mmol) in toluene (0.5 mL). The solution was stirred at ambient temperature for 15 minutes during which time the color changed from red-brown to bright green. After approximately 30 minutes a green precipitate formed. Pentane was added to further precipitate the product. The mother liquor was decanted and the green solid was washed 3 times with pentane (2 mL) and dried in vacuo to yield (9) (0.040 g, 92%).

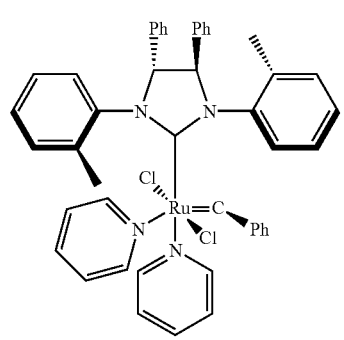

(9)

$[\alpha]^{22}_D$ −45.0° (c 0.005, $CH_2Cl_2$). $^1H$ NMR (300 MHz, $CDCl_3$) exists as a mixture of atropisomers (2.5:1): δ 1.73 (s, $ArCH_3$, 3H), 2.66 (s, $ArCH_3$, 3H), 2.78 (s, $ArCH_3$, 3H), 2.97 (s, $ArCH_3$, 3H), 5.29 (d, J=4 Hz, NCHPh, 1H), 2.40 (d, J=7 Hz, NCHPh, 1H), 5.53 (d, J=4 Hz, NCHPh, 1H), 5.74 (d, J=7 Hz, NCHPh, 1H), 6.2-8.6 (ArH, 31H), 9.81 (dd, J=7.5, 1.5, 2H), 9.97 (m, 2H), 19.33 (s, 1H), 19.35 (1H). $^{13}$C NMR (125 MHz, C$^6$D$^6$): δ 219.5 (NCN), 220.5 (NCN), 317.3 (Ru=CHPh), 318.3 (Ru=CHPh). IR(KBr, cm$^{-1}$) 3136, 3107, 3060, 3028, 2934, 2876, 1492 (s), 1445 (s), 1378 (s), 1249 (s), 1220 (s), 756 (s), 706 (s). Anal. calculated for C$_{46}$H$_{42}$Cl$_2$N$_4$Ru: C, 67.15; H, 5.14; N, 6.81. Found C, 67.24; H, 5.29; N, 6.80.

Example 5

Representative Procedure for the Desymmetrization of Achiral Trienes

Having synthesized a series of catalysts, the enantioselective desymmetrization of substrates (10), (11), and (12) to dihydrofurans (13), (14), and (15), respectively, was effected by the following scheme:

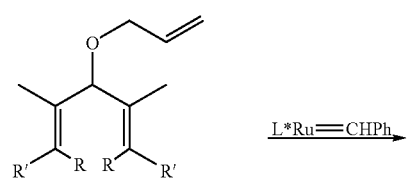

(10) R = H, R' = H
(11) R = Me, R' = H
(12) R = H, R' = Me

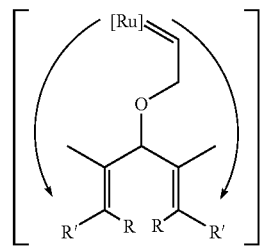

(13) R = H, R' = H
(14) R = Me, R' = H
(15) R = H, R' = Me

In a 10 mL Schlenk flask on the bench top, tetrahydrofuran (2.0 mL) was added to catalyst 8c (0.0050 g, 0.0050 mmol). Sodium iodide (0.015 g, 0.100 mmol) was added and the solution was stirred at ambient temperature for 1 hour. All of the salts were observed to dissolve and the color turned from reddish-brown to brown. Substrate (11) (0.020 g, 0.11 mmol) and toluene (10 μL internal standard) were added via syringe and the solution was heated at 35° C. for 2 hours after which time the solution darkened considerably. An aliquot was taken and analyzed by chiral GC for enantiomeric excess and conversion.

Substrates (10), (11), and (12) monosubstituted central olefin with which the catalyst undergoes the initial metathesis reaction (Ulman et al., *Organometallics* 17:2484-2489 (1998)), and two di- or trisubstituted pendant olefins with which the stereochemically defining cyclization step occurs.

Example 6

Enantioselective Desymmetrization Reactions

A preliminary series of reactions, the desymmetrization of substrate (10), reveals three distinct trends in catalyst selectivity (Table 1). First, catalysts prepared from (1R,2R)-diphenylethylenediamine (8a, 8b, 8c) exhibit higher enantioselectivity (up to 23% ee) than those prepared from (1R,2R)-1,2-diaminocyclohexane (7a, 7b, 7c) (<9% ee). Second, replacement of the mesityl groups (8a, 15% ee, entry 1) with o-methyl- (8b, 23% ee, entry 2) or o-isopropylaryl groups (8c, 23% ee, entry 3) increases the enantioselectivity. Third, changing the halide ligands of catalyst (8c) from Cl— (23% ee, entry 3) to I— (39% ee, entry 5) further improves the enantioselectivity. Although the enantioselectivity increases upon changing to the iodide, a marked reduction in the conversion to 13 is observed, presumably due to the instability of the diiodoruthenium methylidene complex (Ulman et al., *J. Org. Chem.* 64:7202-7207 (1999) generated in the course of this reaction.

The conditions were as follows: 2.5 mol % of catalyst, 55 mM substrate in CH$_2$Cl$_2$, 38°. When the halide salt was included, conditions were: 5 mol % of catalyst, 100 mol % of halide salt, 55 mM substrate in THF, 38° C.

TABLE 1

Enantioselective Desymmetrization of Trienes 10, 11, and 12 by Catalysts 8a, 8b and 8c

| Entry | Substrate | Catalyst | Product | ee (%)[a] | K$_{rel}$ | conversion (%)[b] |
|---|---|---|---|---|---|---|
| 1 | (10) | (8a) | (S-13) | 13 | 1.3 | 57 |
| 2 | (10) | (8b) | (S-13) | 23 | 1.6 | 95 |
| 3 | (10) | (8c) | (S-13) | 23 | 1.6 | 96 |
| a | (10) | (8a) + NaI | (S-13) | 5 | — | 28 |
| 4 | (10) | (8b) + NaI | (S-13) | 38 | 2.2 | 18 |
| 5 | (10) | (8c) + NaI | (S-13) | 39 | 2.2 | 20 |
| b | (11) | (8a) | (S-14) | <2 | — | 65 |
| c | (11) | (8b) | (S-14) | <2 | — | 80 |
| d | (11) | (8c) | (S-14) | 12 | — | 97 |
| e | (11) | (8a) + NaI | (S-14) | <2 | — | 43 |
| 6 | (11) | (8b) + NaI | (S-14) | 17 | 1.4 | 78 |
| 7 | (11) | (8c) + NaI | (S-14) | 35 | 2.1 | 90 |
| f | (12) | (8a) | (S-15) | 15 | — | 67 |
| g | (12) | (8b) | (S-15) | 28 | — | 64 |
| h | (12) | (8c) | (S-15) | 35 | — | 82 |
| i | (12) | (8a) + NaI | (S-15) | 17 | — | 78 |
| 8 | (12) | (8b) + LiBr | (S-15) | 63 | 4.4 | 90 |
| 9 | (12) | (8b) + NaI | (S-15) | 85 | 12.3 | 91 |
| 10 | (12) | (8c) + LiBr | (S-15) | 69 | 5.5 | 90 |
| 11 | (12) | (8c) + NaI | (S-15) | 90 | 19 | 82 |

[a]Absolute stereochemistry determined by comparison with GLC chromatograms reported in La et al., J. Am. Chem. Soc. 120:9720-9721 (1998).
[b]Measured by chiral GLC (Chiraldex GTA Alltech) with toluene as an internal standard.

Similar conditions were used to evaluate catalysts 7a, 7b and 7c.

TABLE 2

Enantioselective Desymmetrization of
Trienes 10, 11, and 12 by Catalysts 7a, 7b and 7c

| Entry | Substrate | Catalyst | ee (%)[a] | conversion (%) |
|---|---|---|---|---|
| 1 | (10) | (7a) | 8 | 93 |
| 2 | (10) | (7b) | 3 | >95 |
| 3 | (10) | (7c) | 5 | >95 |
| 4 | (10) | (7a) + NaI | 5 | 20 |
| 5 | (10) | (7b) + NaI | 5 | 46 |
| 6 | (10) | (7c) + NaI | 5 | 42 |
| 7 | (11) | (7a) | 4 | >95 |
| 8 | (11) | (7b) | 5 | 44 |
| 9 | (11) | (7c) | 6 | 94 |
| 10 | (11) | (7a) + NaI | 1 | >95 |
| 11 | (11) | (7b) + NaI | 5 | >95 |
| 12 | (11) | (7c) + NaI | 10 | >95 |
| 13 | (12) | (7a) | 9 | >95 |
| 14 | (12) | (7b) | 0 | >95 |
| 15 | (12) | (7c) | 11 | >95 |
| 16 | (12) | (7a) + NaI | 13 | 20 |
| 17 | (12) | (7b) + NaI | 13 | >95 |
| 18 | (12) | (7c) + NaI | 3 | >95 |

[a] The R enantiomer is the major product in all entries exhibiting significant enantiomeric excess.

Example 7

Evaluation of Substrates 11 and 12

To prevent the generation of the methylidene complex and to explore the substrate requirements for high enantioselectivity, trisubstituted substrates 11 and 12 were tested. In the case of the (Z)-trisubstituted olefin 11, conversions were always high, but enantioselectivities were relatively low (<36% ee). However, in the case of (E)-trisubstituted olefin 12, high enantioselectivity and high conversion were achieved (90% ee, entry 11). Importantly, neither solvent (THF, dichloromethane, benzene) nor temperature (−15° C., 0° C., 38° C.) had a significant effect on the enantioselectivity of these systems. Additionally, the activity and stability of catalysts 8b and 8c are similar to those of the IMesH$_2$/ruthenium system (rigorous exclusion of air and moisture is not required).

Example 8

Stereochemistry of Dihydrofuran 15

Previous studies suggested a 14-electron, four-coordinate species as the active intermediate in the metathesis cycle (Sanford et al., *J. Am. Chem. Soc.* 123:749-750 (2001)), but the geometry of this intermediate and the subsequent olefin complex intermediates remains unknown. Three different conformations of the intermediate olefin complex have been proposed. See Trnka et al., *Organometallics* 20:3845-3847 (2001); Tallarico et al., *J. Am. Chem. Soc.* 119:7157-7158 (1997); Hinderling et al., *Angew. Chem., Int. Ed.* 37:2685-2689 (1998); Adlhart et al., *J. Am. Chem. Soc.* 122:8204-8214 (2000); Bianchini et al., *Organometallics* 19:1833-1840 (2000); Moers et al., *J. Inorg. Nucl. Chem.* 39:591-593 (1977); Brown et al., *Inorg. Chem.* 17:2932-2935 (1978); and Dias et al., *J. Am. Chem. Soc.* 119:3887-3897 (1997). These three possible geometries of the olefin complex are illustrated as follows:

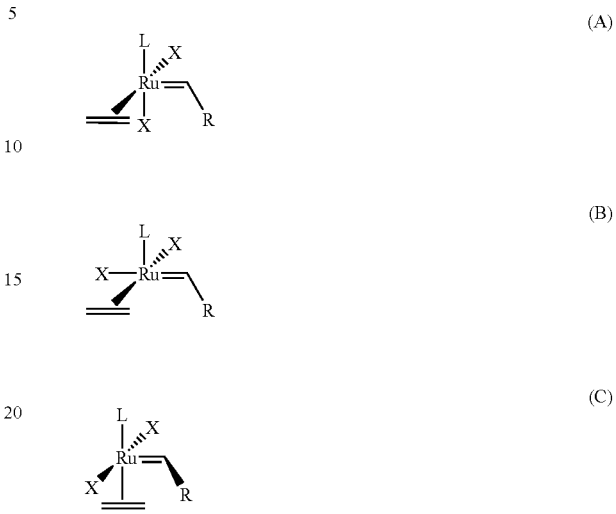

In (A), the halide ligand is bound trans to the L-type ligand. In (B), the halides adopt a cis arrangement in the alkylidene-halide-olefin plane. In (C), the olefin binds trans to the L-type ligand. Of these conformations, only (C) is inconsistent with the observed stereochemical outcome of the desymmetrization of substrates 10, 11 and 12. Although geometry (B) cannot be discounted, geometry (A) appears to be most consistent with the observed ligand effects and stereochemical outcome of these reactions. Geometries similar to that of (A) have been observed crystallographically (Trnka et al., *Organometallics* 20:3845-3847 (2001)) and computationally (Adlhart et al., *J. Am. Chem. Soc.* 122:8204-8214 (2000)) and three key features of stereochemical model (A) are consistent with the observed selectivity. First, the alkylidene substituent is oriented anti to the bulky NHC ligand. Second, the tethered olefin binds to the front face of the complex to avoid a steric interaction with the bulky o-isopropyl group of the NHC ligand. Third, the unbound olefin occupies the distal position relative to the apical halide; this proposed steric interaction between the unbound olefin and apical halide is further consistent with the dramatic increase in enantioselectivity observed upon changing the halide from Cl— to Br— to I—. Further details on the stereochemical model can be found in Seiders, et al., *Organic Letters* 3(20):3225-3228 (2001).

Example 9

Asymmetric Ring Closing Metathesis

To expand the utility of the asymmetric ring closing metathesis reaction, it is desirable to prepare products containing reactive functional groups for potential for further elaboration. The formation of α,β unsaturated carbonyl containing compounds using ruthenium alkylidene catalysts (containing NHC ligands) designate cyclic α, β unsaturated carbonyl containing compounds, i.e. lactones and enones, as potential targets. Using the chiral catalysts described herein, the ability to form functionalized cyclic products in enantioenriched form has been demonstrated.

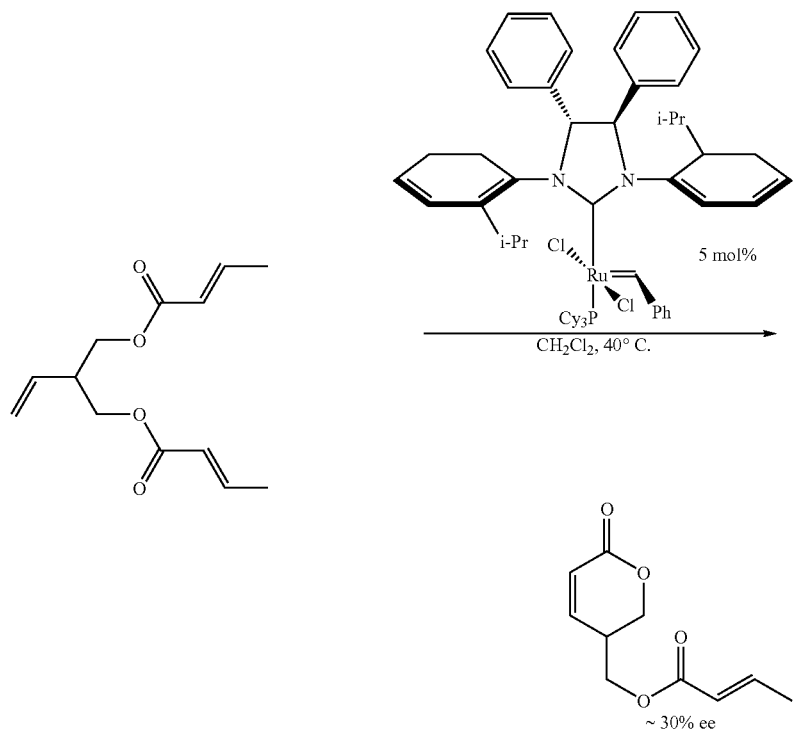

~ 30% ee

Asymmetric cross metathesis provides a powerful means for the formation of stereogenic centers under catalytic and mild conditions starting from readily available olefinic starting materials. In the previously reported desymmetrization reactions, the chiral ligand provides a steric bias that directs the face from which the incoming olefin will approach the catalyst after the substrate is already bound to the catalyst. The enantiomeric excess is then determined by the difference in the relative energies of the two possible cyclic transition states that lead to the cyclic products, not by the initial binding of the substrate. In asymmetric olefin cross metathesis, the ligand not only needs to designate the face from which the cross partner will access the catalyst, but also needs to directly interact with the cross partner during the binding event such that one enantiomer (or one enantiotopic olefin in the case of a desymmetrization) will be preferred. This requires a greater degree of control in the olefin binding event.

The catalysts of the invention effectively impart the desired facial selectivity. It is proposed that inclusion of steric bulk at the meta position, opposite to the ortho group already present, will impart a greater steric influence on the binding of the chiral/prochiral substrates without interfering with the highly effective transmission of chirality from the backbone to the aniline derived aromatic groups.

Example 10

Preparation of Complex 10

Initially, for the ease of synthesis, the catalysts were prepared from commercially available and or readily synthesized starting materials, e.g., 1-bromo-2,5-diisopropylbenzene. Analogous to the preparation of the chiral catalysts described above, palladium mediated coupling of 1-bromo-2,5-diisopropylbenzene to (1R,2R)-diphenyl ethylene diamines afforded the diarylated product in good yield. Conversion to the tetrafluoroborate salt occurred without event. In the formation of the catalyst, and excess of the chiral ligand was employed to ease in the purification.

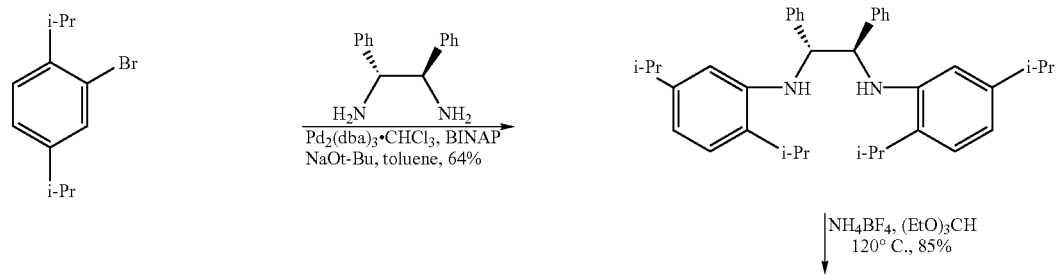

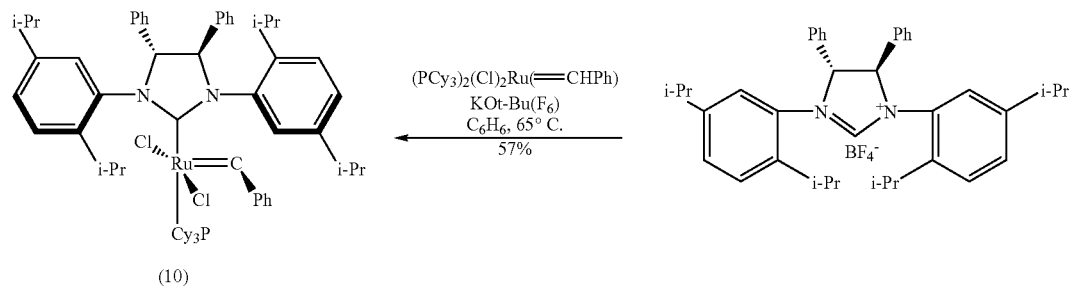
Preliminary data suggests that the tetraisopropyl catalyst 10 is superior for asymmetric olefin cross metathesis and for asymmetric ring closing.
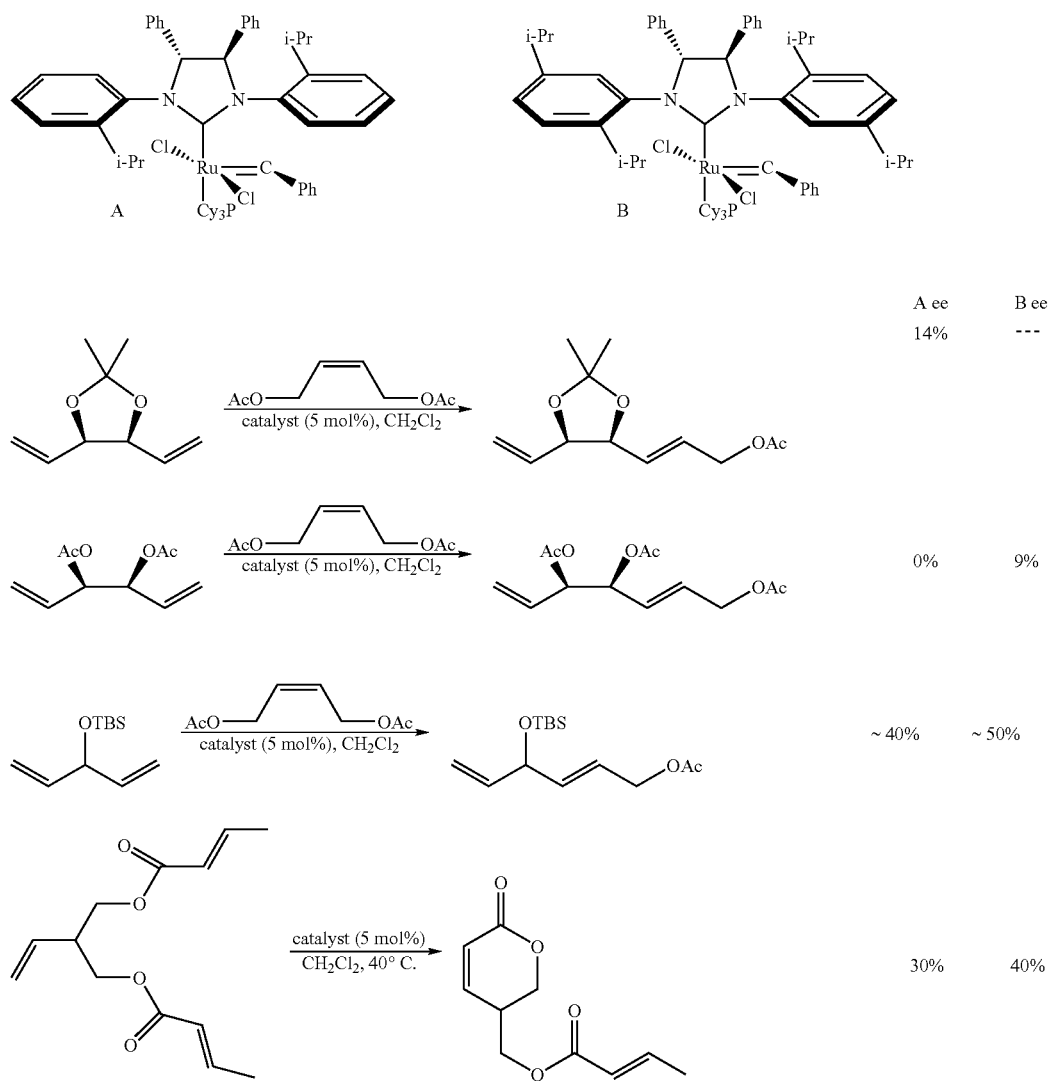

Other examples include the following:

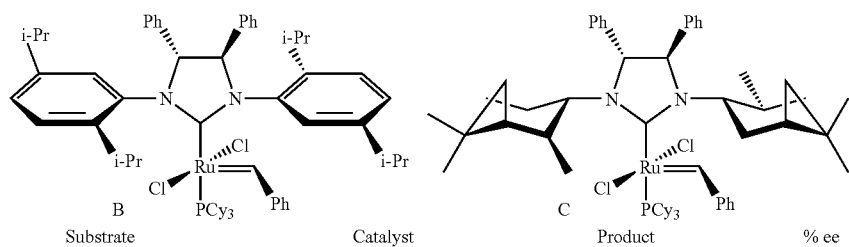

| Substrate | Catalyst | Product | % ee |
|---|---|---|---|

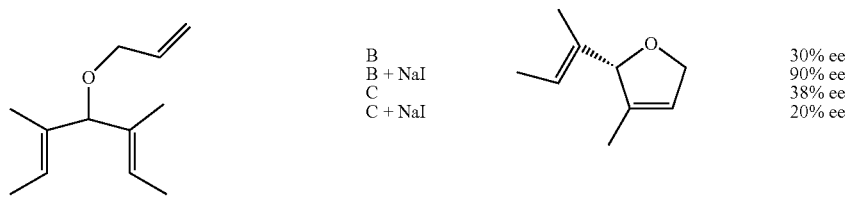

| | B | | 30% ee |
| | B + NaI | | 90% ee |
| | C | | 38% ee |
| | C + NaI | | 20% ee |

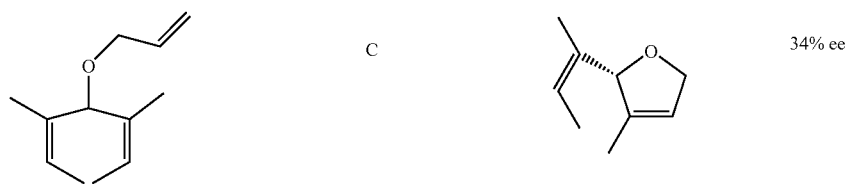

| | C | | 34% ee |

$X^1$ and $X^2$ are independently selected from the group consisting of anionic ligands and a linker attached to a polymeric substrate, or $X^1$ and $X^2$ may be taken together to form a cyclic group;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxyl;

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group;

$Y^1$ and $Y^2$ are heteroatoms independently selected from the group consisting of N, O, S, and P, with the proviso that when $Y^1$ or $Y^2$ is O or S, then the appended aryl group is absent;

$R^5$ and $R^6$ define chiral centers at the ring carbons and are independently selected from the group consisting of a linker attached to a polymeric substrate, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

$R^{20}$ and $R^{21}$ are independently selected from the group consisting of hydrogen, $C_{1-20}$ alkyl, substituted $C_{1-20}$ alkyl, perfluoronated $C_{1-20}$ alkyl, $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl, $C_{5-30}$ alkaryl, and halo; and L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether.

The invention claimed is:

1. A chiral Group 8 transition metal carbene complex comprising the formula:

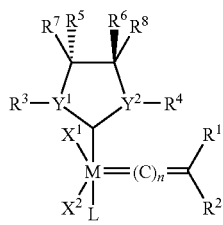

wherein:

M is a Group 8 transition metal;

$X^1$ and $X^2$ are independently selected from the group consisting of anionic ligands and a linker attached to a polymeric substrate, or $X^1$ and $X^2$ may be taken together to form a cyclic group;

n is 0;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxy;

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group;

$Y^1$ and $Y^2$ are heteroatoms independently selected from the group consisting of N, O, S, and P, with the proviso that when $Y^1$ or $Y^2$ is O or S, then $R^3$ or $R^4$ is absent;

$R^3$ and $R^4$ are independently selected from the group consisting of hydrogen, functional groups, hydrocarbyl, substituted hydrocarbyl, heteroatom-containing hydrocarbyl, substituted heteroatom- containing hydrocarbyl, and a linker attached to polymeric substrate;

$R^5$, $R^6$, $R^7$, and $R^8$ define chiral centers at the ring carbons and are independently selected from the group consisting of a linker attached to a polymeric substrate, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether, and may or may not be linked to $R^2$, $X^1$, and/or $X^2$ through a spacer moiety; and wherein any two or more of $X^1$, $X^2$, L, $R^1$, $R^2$, $R^3$, $R^4$, $R^5$, $R^6$, $R^7$, and $R^8$ can be taken together to form a chelating multidentate ligand.

2. The complex of claim 1 wherein M is selected from the group consisting ruthenium and osmium.

3. The complex of claim 2 wherein M is ruthenium.

4. The complex of claim 1 wherein $X^1$ and $X^2$ are taken together to form a 5- to 8-membered cyclic group.

5. The complex of claim 1 wherein $X^1$ and $X^2$ are independently selected from the group consisting of hydrogen, halo, $C_{1-20}$ alkyl, $C_{5-20}$ aryl, $C_{1-20}$ alkoxy, $C_{5-20}$ aryloxy, $C_{3-20}$ alkyldiketonate, $C_{5-20}$ aryldiketonate, $C_{2-20}$ alkoxycarbonyl, $C_{5-20}$ aryloxycarbonyl, $C_{2-20}$ acyl, $C_{1-20}$ alkylsulfonato, $C_{5-20}$arylsulfonato, $C_{1-20}$ alkylsulfanyl, $C_{5-20}$ arylsulfanyl, $C_{1-20}$ alkylsulfinyl, and $C_{5-20}$ arylsulfinyl.

6. The complex of claim 5 wherein at least one of $X^1$ and $X^2$ is substituted with one or more moieties selected from the group consisting of $C_{1-10}$ alkyl, $C_{1-10}$ alkoxy, $C_{5-20}$ aryl, and halo.

7. The complex of claim 5 wherein $X^1$ and $X^2$ are independently selected from the group consisting of halo, benzoate, $C_{2-6}$ acyl, $C_{2-6}$ alkoxycarbonyl, $C_{1-6}$ alkyl, phenoxy, $C_{1-6}$ alkoxy, $C_{1-6}$alkylsulfanyl, $C_{5-20}$ aryl, and $C_{1-6}$ alkylsulfonyl.

8. The complex of claim 7 wherein $X^1$ and $X^2$ are independently selected from the group consisting of halo, $CF_3CO_2$, $CH_3CO_2$, $CFH_2CO_2$, $(CH_3)_3CO$, $(CF_{32}(CH_3)CO$, $(CF_3)(CH_3)_2CO$, PhO, MeO, EtO, tosylate, mesylate, and trifluoromethanesulfonate.

9. The complex of claim 8 wherein $X^1$ and $X^2$ are halo.

10. The complex of claim 1 wherein $R^1$ is selected from the group consisting of hydrogen and $C_{5-20}$ aryl.

11. The complex of claim 1 wherein $R^2$ is selected from the group consisting of $C_{1-20}$ alkyl, $C_{2-20}$ alkenyl, and $C_{5-20}$ aryl.

12. The complex of claim 11 wherein $R^2$ is selected from the group consisting of phenyl, vinyl, methyl, isopropyl and t-butyl.

13. The complex of claim 12 wherein $R^2$ is substituted with one or more moieties selected from the group consisting of $C_{1-6}$ alkyl, $C_{1-6}$ alkoxy, phenyl, and a functional group.

14. The complex of claim 13 wherein $R^2$ is phenyl or vinyl substituted with one or more moieties selected from the group consisting of chloro, bromo, iodo fluoro, nitro, dimethylamino, methyl, methoxy, and phenyl.

15. A chiral Group 8 transition metal carbene complex comprising the formula:

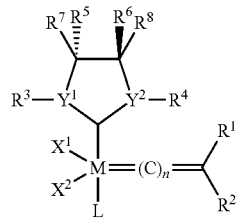

wherein:

M is a Group 8 transition metal;

$X^1$ and $X^2$ are independently selected from the group consisting of anionic ligands and a linker attached to a polymeric substrate, or $X^1$ and $X^2$ may be taken together to form a cyclic group;

n is an integer from 0-5;

$R^1$ is selected from the group consisting of hydrogen, silyl, hydrocarbyl, substituted hydrocarbyl, heteroatom-containing hydrocarbyl, substituted heteroatom-containing and carboxy;

$R^2$ is selected from the group consisting of phenyl and —C=C(CH$_3$)$_2$;

$Y^1$ and $Y^2$ are heteroatoms independently selected from the group consisting of N, O, S, and P, with the proviso that when $Y^1$ or $Y^2$ is O or S, then $R^3$ or $R^4$ is absent;

$R^3$ and $R^1$ are independently selected from the group consisting of hydrogen, functional groups, hydrocarbyl, substituted hydrocarbyl, heteroatom-containing hydrocarbyl, substituted heteroatom- containing hydrocarbyl, and a linker attached to polymeric substrate;

$R^5$, $R^6$, $R^7$, and $R^8$ define chiral centers at the ring carbons and are independently selected from the group consisting of a linker attached to a polymeric substrate, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether, and may or may not be linked to $R^2$, $X^1$, and/or $X^2$ through a spacer moiety; and wherein any two or more of $X^1$, $X^2$, L, $R^1$, $R^2$, $R^3$, $R^4$, $R^5$, $R^6$, $R^7$, and $R^8$ can be taken together to form a chelating multidentate ligand.

16. The complex of claim 1 wherein $R^1$ and $R^2$ are taken together to form a 5- to 8-membered cyclic group.

17. The complex of claim 1 wherein $Y^1$ and $Y^2$ are the same heteroatom.

18. The complex of claim 1 wherein $Y^1$ and $Y^2$ are N.

19. The complex of claim 1 wherein at least one of $R^1$ and $R^4$ is a functional group.

20. The complex of claim 19 wherein the functional group is acyl.

21. The complex of claim 1 wherein $R^3$ and $R^4$ are independently selected from the group consisting of $C_{5-20}$ aryl, hydrocarbyl-substituted $C_{5-20}$ aryl, and hydrocarbyl-substituted heteroaryl.

22. The complex of claim 1 wherein at least one of $R^3$ and $R^4$ is selected from the group consisting of alicycic and aromatic structures having 1-5 rings.

23. The complex of claim 22 wherein both $R^3$ and $R^4$ are selected from the group consisting of alicyclic and aromatic structures having 1-5 rings.

24. The complex of claim 23 wherein $R^3$ and $R^4$ are independently selected from the group consisting of $C_{5-20}$ aryl, substituted aryl, heteroaryl, substituted heteroaryl, alicycic, and substituted alicyclic.

25. A chiral Group 8 transition metal carbene complex comprising the formula:

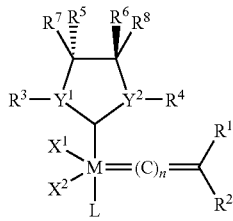

wherein:

M is a Group 8 transition metal;

$X^1$ and $X^2$ are independently selected from the group consisting of anionic ligands and a linker attached to a polymeric substrate, or $X^1$ and $X^2$ may be taken together to form a cyclic group;

n is an integer from 0-5;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxy;

$R^2$ is selected from the group consisting of hydrogen, silyl, hydrocarbyl, substituted hydrocarbyl, heteroatom-containing hydrocarbyl, and substituted heteroatom-containing hydrocarbyl, or $R^1$ and $R^2$ may be taken together to form a cyclic group;

$Y^1$ and $Y^2$ are heteroatoms independently selected from the group consisting of N, O, S, and P, with the proviso that when $Y^1$ or $Y^2$ is O or S, then $R^3$ or $R^4$ is absent;

$R^3$ and $R^4$ are independently selected from the group consisting of hydrogen, functional groups, hydrocarbyl, substituted hydrocarbyl, heteroatom-containing hydrocarbyl, substituted heteroatom- containing hydrocarbyl, and a linker attached to polymeric substrate and at least one of $R^3$ and $R^4$ is a nitrogen-containing heterocycle;

$R^5$, $R^6$, $R^7$, and $R^8$ define chiral centers at the ring carbons and are independently selected from the group consisting of a linker attached to a polymeric substrate, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether, and may or may not be linked to $R^2$, $X^1$, and/or $X^2$ through a spacer moiety; and wherein any two or more of more of $X^1$, $X^2$, L, $R^1$, $R^2$, $R^3$, $R^4$, $R^5$, $R^6$, $R^7$, and $R^8$ can be taken together to form a chelating multidentate ligand.

26. The complex of claim 24 wherein $R^3$ and $R^4$ are $C_{5-20}$ aryl and have one or two aromatic rings.

27. The complex of claim 26 wherein $R^3$ and $R^4$ each have the structure:

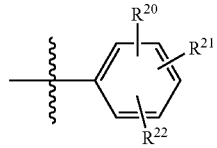

wherein $R^{20}$, $R^{21}$, and $R^{22}$ are independently selected from the group consisting of hydrogen, $C_{1-20}$ alkyl, substituted $C_{1-20}$ alkyl, perfluoronated $C_{1-20}$ alkyl, $C_{1-20}$ heteroalkyl, substituted $C_{1-20}$ heteroalkyl $C_{1-20}$ alkoxy, $C_{5-20}$ aryl, substituted $C_{5-20}$ aryl, heteroaryl, $C_{5-30}$ aralkyl, $C_{5-30}$ alkaryl, and halo.

28. The complex of claim 27 wherein $R^{20}$, $R^{21}$, and $R^{22}$ are independently selected from the group consisting of hydrogen, methyl, ethyl, propyl, isopropyl, hydroxyl, halo, phenyl, and lower alkyl-substituted phenyl.

29. The complex of claim 27 wherein $R^{20}$, $R^{21}$, and $R^{22}$ are methyl.

30. The complex of claim 26 wherein $R^3$ and $R^4$ are independently selected from the group consisting of biphenylyl and substituted biphenylyl.

31. The complex of claim 23 wherein $R^3$ and $R^4$ are $C_{7-20}$ alicyclic.

32. The complex of claim 31 wherein $R^3$ and $R^4$ are $C_{7-12}$ alicyclic.

33. The complex of claim 1 wherein $R^5$, $R^6$, $R^7$, and $R^8$ are independently selected from the group consisting of hydrogen, $C_{1-10}$ alkyl, $C_{5-20}$ aryl, cyclohexyl, mesityl, and lower alkyl substituted phenyl.

34. A chiral Group 8 transition metal carbene complex comprising the formula:

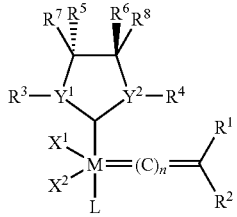

wherein:

M is a Group 8 transition metal;

$X^1$ and $X^2$ are independently selected from the group consisting of anionic ligands and a linker attached to a polymeric substrate, or $X^1$ and $X^2$ may be taken together to form a cyclic group;

n is an integer from 0-5;

$R^1$ is selected from the group consisting of hydrogen, silyl, hydrocarbyl, substituted hydrocarbyl, heteroatom-containing hydrocarbyl, substituted heteroatom-containing hydrocarbyl, and carboxy;

R² is selected from the group consisting of hydrogen, silyl, hydrocarbyl, substituted hydrocarbyl, heteroatom-containing hydrocarbyl, and substituted heteroatom-containing hydrocarbyl, or R¹ and R² may be taken together to form a cyclic group;

Y¹ and Y² are heteroatoms independently selected from the group consisting of N, O, S, and P, with the proviso that when Y¹ or Y² is O or S, then R³ or R⁴ is absent;

R³ and R⁴ are independently selected from the group consisting of hydrogen, functional groups, hydrocarbyl, substituted hydrocarbyl, heteroatom-containing hydrocarbyl, substituted heteroatom- containing hydrocarbyl, and a linker attached to polymeric substrate;

$R^5$, $R^6$, $R^7$, and $R^8$ define chiral centers at the ring carbons and are independently selected from the group consisting of a linker attached to a polymeric substrate, hydrogen hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

L is a nitrogen-containing heterocycle and may or may not be linked to $R^2$, $X^1$, and/or $X^2$ through a spacer moiety; and wherein any two or more of $X^1$, $X^2$, L, $R^1$, $R^2$, $R^3$, $R^4$, $R^5$, $R^6$, $R^7$ and $R^8$ can be taken together to form a chelating multidentate ligand.

35. The complex of claim 1 wherein L and R² are linked together.

36. The complex of claim 1 wherein L is linked to X¹ or to X².

37. The complex of claim 1 wherein L is linked to both X¹ and X².

38. The complex of claim 1 which is attached to a linker attached to a polymeric substrate.

39. The complex of claim 38 wherein at least one of X¹ and X² is a linker attached to a polymeric substrate.

40. The complex of claim 38 wherein at least one of R³ and R⁴ is a linker attached to a polymeric substrate.

41. The complex of claim 38 wherein at least one of $R^5$, $R^6$, $R^7$, and $R^8$ is a linker attached to a polymeric substrate.

42. The complex of claim 1 which further comprises a neutral electron donor ligand attached to the Group 8 transition metal.

43. A chiral ruthenium carbene complex of the formula:

wherein:

X¹ and X² are independently selected from the group consisting or anionic ligands and a linker attached to a polymeric substrate, or X¹ and X² may be taken together to form a cyclic group;

R¹ is selected from the group consisting of hydrogen, silyl, hydrocarbyl, substituted hydrocarbyl, heteroatom-containing hydrocarbyl, substituted heteroatom-containing hydrocarbyl, and carboxyl;

R² is selected from the group consisting of hydrogen, silyl, hydrocarbyl, substituted hydrocarbyl, heteroatom-containing hydrocarbyl, and substituted heteroatom-containing hydrocarbyl, or R¹ and R² may be taken together to form a cyclic group;

Y¹ and Y² are heteroatoms independently selected from the group consisting of N, O, S, and P, with the proviso that when Y¹ or Y² is O or S, then the appended aryl group is absent;

$R^5$ and $R^6$ define chiral centers at the ring carbons and are independently selected from the group consisting of a linker attached to a polymeric substrate, hydrocarbyl, substituted hydrocarbyl, heteroatom-containing hydrocarbyl, substituted heteroatom-containing hydrocarbyl, and functional groups, optionally substituted with one or more moieties selected from the group consisting of $C_{1-10}$ alkyl, $C_{1-10}$ alkoxy, $C_{5-20}$ aryl, hydroxyl, sulfhydryl, —(CO)—H, halo, and functional groups;

$R^{20}$ and $R^{21}$ are independently selected from the group consisting of hydrogen, $C_{1-10}$ alkyl, substituted $C_{1-20}$ alkyl, perfluoronated $C_{1-20}$ alkyl, $C_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl, $C_{5-30}$ alkaryl, and halo; and L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether.

44. The complex of claim 43 wherein X¹ and X² are independently selected from the group consisting of halo, benzoate, $C_{2-6}$ acyl, $C_{2-6}$ alkoxycarbonyl, $C_{1-6}$ alkyl, phenoxy, $C_{1-6}$ alkoxy, $C_{1-6}$ alkylsulfanyl, $C_{5-20}$ aryl, and $C_{1-6}$ alkylsulfonyl.

45. The complex of claim 44 wherein X¹ and X² are independently selected from the group consisting of halo, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

46. The complex of claim 45 wherein X¹ and X² are halo.

47. The complex of claim 43 wherein R¹ is selected from the group consisting of hydrogen and $C_{5-20}$ aryl.

48. The complex of claim 43 wherein R² is $C_{5-20}$ aryl.

49. The complex of claim 48 wherein R² is phenyl.

50. The complex of claim 43 wherein Y¹ and Y² are N.

51. The complex of claim 43 wherein $R^5$ and $R^6$ are $C_{5-20}$ aryl.

52. The complex of claim 43 wherein $R^{20}$ is alkyl, and $R^{21}$ is hydrogen.

53. The complex of claim 43 wherein $R^{20}$ and $R^{21}$ are alkyl.

54. The complex of claim 43 wherein L is selected from the group consisting of phosphine, sulfonated phosphine, phosphite, phosphinite, phosphonite, arsine, stibine, ether, amino, amido, imino, sulfoxide, carboxy, nitrosyl, pyridyl, substituted pyridyl, imidazolyl, substituted imidazolyl, pyrazinyl, and thioether.

55. The complex of claim 54 wherein L is a phosphine having the formula PR'R"R'", where R', R", and R'" are each independently selected from the group consisting of $C_{1-10}$ alkyl, $C_{5-20}$ aryl, and a heteroatom-containing functional group.

56. The complex of claim 55 wherein R', R", and R'" are the same.

57. The complex of claim 56 wherein L is selected from the group consisting of —P(cyclohexyl)$_3$, —P(cyclopentyl)$_3$, —P(isopropyl)$_3$, and —P(phenyl)$_3$.

58. The complex of claim 55 wherein L is a phosphine having the formula —P(phenyl)$_2$(R) or —P(phenyl)(R)$_2$, where R is C$_{1-20}$ alkyl.

59. A method of controlling the enantioselectivity of an olefin metathesis reaction comprising catalyzing the reaction with a chiral Group 8 transition metal carbene complex of the formula:

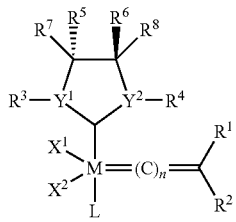

wherein:
M is a Group 8 transition metal;
X$^1$ and X$^2$ are independently selected from the group consisting of anionic ligands and a linker attached to a polymeric substrate, or X$^1$ and X$^2$ may be taken together to form a cyclic group;
n is an integer from 0-5;
R$^1$ is selected from the group consisting of hydrogen, silyl, hydrocarbyl, substituted hydrocarbyl, heteroatom-containing hydrocarbyl, substituted heteroatom-containing hydrocarbyl, and carboxy;
R$^2$ is selected from the group consisting of hydrogen, silyl, hydrocarbyl, substituted hydrocarbyl, heteroatom-containing hydrocarbyl, and substituted heteroatom-containing hydrocarbyl, or R$^1$ and R$^2$ may be taken together to form a cyclic group;
Y$^1$ and Y$^2$ are heteroatoms independently selected from the group consisting of N, O, S, and P, with the proviso that when Y$^1$ or Y$^2$ is O or S, then R$^3$ or R$^4$ is absent;
R$^3$ and R$^4$ are independently selected from the group consisting of hydrogen, functional groups, hydrocarbyl, substituted hydrocarbyl, heteroatom-containing hydrocarbyl, and substituted heteroatom-containing hydrocarbyl;
R$^5$, R$^6$, R$^7$, and R$^8$ define chiral centers at the ring carbons and are independently selected from the group consisting of a linker attached to a polymeric substrate, hydrogen, hydrocarbyl, substituted hydrocarbyl, heteroatom-containing hydrocarbyl, substituted heteroatom-containing hydrocarbyl, and functional groups, optionally substituted with one or more moieties selected from the group consisting of C$_{1-10}$ alkyl, C$_{1-10}$ alkoxy, C$_{5-20}$ aryl, hydroxyl, sulfhydryl, —(CO)—H, halo, and functional groups;
L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether, and may or may not be linked to R$^2$, X$^1$, and/or X$^2$ through a spacer moiety; and wherein any two or more of X$^1$, X$^2$, L, R$^1$, R$^2$, R$^3$, R$^4$, R$^5$, R$^6$, R$^7$, and R$^8$ can he taken together to form a chelating multidentate ligand.

60. The method of claim 59 wherein the olefin metathesis reaction is the enantioselective desymmetrization of meso-trienes.

61. The method of claim 59 wherein the olefin metathesis reaction is the enantioselective desymmetrization of achiral trienes.

62. The method of claim 59 wherein the olefin metathesis reaction is the enantioselective desymmetrization of meso-dienes.

63. The method of claim 59 wherein the olefin metathesis reaction is the enantioselective desymmetrization of achiral dienes.

64. The method of claim 59 wherein the olefin metathesis reaction is an enantioselective ring-opening/ring-c losing metathesis.

65. The method of claim 59 wherein the olefin metathesis reaction is an enantioselective ring-opening/cross metathesis.

66. The method of claim 59 wherein the olefin metathesis reaction is the kinetic resolution of racemic mixtures of chiral olefins.

67. The method of claim 65 which further comprises treating the complex with a reagent of the formula NaX, where X is a negatively charged counterion.

68. The method of claim 67 wherein X is selected from the group consisting of Br$^-$ and I$^-$.

69. The method of claim 59 wherein the Group 8 transition metal carbene complex has the formula:

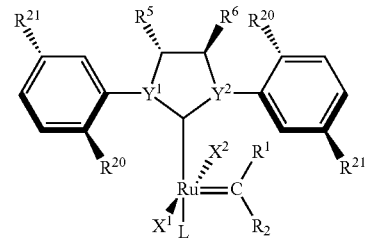

wherein:
X$^1$ and X$^2$ are independently selected from the group consisting of anionic ligands and a linker attached to a polymeric substrate, or X$^1$ and X$^2$ may be taken together to form a cyclic group;
R$^1$ is selected from the group consisting of hydrogen, silyl, hydrocarbyl, substituted hydrocarbyl, heteroatom-containing hydrocarbyl, substituted heteroatom-containing hydrocarbyl, and carboxyl;
R$^2$ is selected from the group consisting of hydrogen, silyl, hydrocarbyl, substituted hydrocarbyl, heteroatom-containing hydrocarbyl, and substituted heteroatom-containing hydrocarbyl, or R$^1$ and R$^2$ may be taken together to form a cyclic group;
Y$^1$ and Y$^2$ are heteroatoms independently selected from the group consisting of N, O, S, and P, with the proviso that when Y$^1$ or Y$^2$ is O or S, then the appended aryl group is absent;
R$^5$ and R$^6$ define chiral centers at the ring carbons and are independently selected from the group consisting of a linker attached to a polymeric substrate, hydrocarbyl, substituted hydrocarbyl, heteroatom-containing hydrocarbyl, substituted heteroatom-containing hydrocarbyl, and functional groups, optionally substituted with one or more moieties selected from the group consisting of C$_{1-10}$ alkyl, C$_{1-10}$ alkoxy, C$_{5-20}$ aryl, hydroxyl, sulfhydryl, —(CO)—H, halo, and functional groups;
R$^{20}$ and R$^{21}$ are independently selected from the group consisting of hydrogen, C$_{1-20}$ alkyl, substituted C$_{1-20}$ alkyl, perfluoronated C$_{1-20}$ alkyl, C$_{1-20}$ heteroalkyl, substituted $C_{1-20}$ heteroalkyl, $C_{1-20}$ alkoxy, $C_{5-20}$ aryl, substituted $C_{5-20}$ aryl, heteroaryl, $C_{5-30}$ aralkyl $C_{5-30}$ alkaryl, and halo; and L is selected from the group consisting of arsine, stibine, ether, amino, amido, imino, sulfoxide, carboxy, nitrosyl, pyridyl, substituted pyridyl, imidazolyl, substituted imidazolyl, pyrazinyl, and thioether.

* * * * *